(12) United States Patent
Rieske-Kinney et al.

(10) Patent No.: US 11,230,714 B2
(45) Date of Patent: Jan. 25, 2022

(54) GENE SILENCING KILLS EMERALD ASH BORER, AN EXOTIC, INVASIVE TREE-KILLING INSECT

(71) Applicant: University of Kentucky Research Foundation, Lexington, KY (US)

(72) Inventors: Lynne Rieske-Kinney, Lexington, KY (US); Thais Barros Rodrigues, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 16/827,270

(22) Filed: Mar. 23, 2020

(65) Prior Publication Data
US 2020/0299695 A1    Sep. 24, 2020

Related U.S. Application Data

(60) Provisional application No. 62/822,356, filed on Mar. 22, 2019.

(51) Int. Cl.
C12N 15/113    (2010.01)

(52) U.S. Cl.
CPC ........ *C12N 15/113* (2013.01); *C12N 2310/14* (2013.01)

(58) Field of Classification Search
CPC ............ C12N 2320/31; C12N 2310/14; C12N 15/113
See application file for complete search history.

(56) References Cited

PUBLICATIONS

Pampolini and Rieke (Frontiers in Agronomy, 2020 vol. 2:1-11, plus Supplementary Tables 1 and 2).*
Ghosh et al. (BMC Genomics, 2014 vol. 15:1-23).*
Rodrigues, et al., Identification of highly effective target genes for RNAi-mediated control of emerald ash borer, Agrilus planipennis, Scientific Reports | (2018) 8:5020, pp. 1-9.
Rodrigues, et al., RNAi technology to manage emerald ash borer (Presentation); 2017 pp. 1-15.
Rodrigues, et al., RNAi technology to manage emerald ash borer (Abstract), Nov. 7, 2017.
Rodrigues, et al., Development of RNAi method for screening candidate genes to control emerald ash borer, Agrilus planipennis, Scientific Reports 2017: 7379.
Andrade, E. C. & Hunter, W. B. RNAi feeding bioassay: development of a non-transgenic approach to control Asian citrus psyllid and other hemipterans. Entomol Exp Appl 162, 389 396, https://doi.org/10.1111/eea.12544 (2017).
Galdeano, D. M., Breton, M. C., Lopes, J. R. S., Falk, B. W. & Machado, M. A. Oral delivery of double-stranded RNAs induces mortality in nymphs and adults of the Asian citrus psyllid, Diaphorina citri. Plos One 12, e0171847,https://doi.org/10.1371/journal. pone. 0171847 (2017).

(Continued)

*Primary Examiner* — Terra C Gibbs
(74) *Attorney, Agent, or Firm* — Stites & Harbison PLLC; Mandy Wilson Decker; Gary N. Stewart

(57) ABSTRACT

The presently-disclosed subject matter generally relates to RNAi-based methods and compositions for pest control of the highly invasive Emerald Ash Borer. The disclosed matter also relates to a composition which includes dsRNA directed towards target genes and a method of administering said composition.

7 Claims, 11 Drawing Sheets

Specification includes a Sequence Listing.

(56) References Cited

PUBLICATIONS

Leelesh, RS, LK Rieske. Bacterially expressed dsRNA can silence genes and cause mortality in a highly invasive, tree-killing pest, the emerald ash borer (EAB), Agrilus planipennis. Insects 11(7), 440; https://doi.org/10.3390/insects11070440 (2020).

Pampolini, FB, TB Rodrigues, RS Leelesh, T Kawashima, LK Rieske. Confocal microscopy provides visual evidence and confirms the feasibility of dsRNA delivery to emerald ash borer through plant tissues. Journal of Pest Science DOI:10.1007/s10340-020-01230-w (2020).

Rajarapu, S. P., Mamidala, P. & Mittapalli, O. Validation of reference genes for gene expression studies in the emerald ash borer (*Agrilus planipennis*). Insect Sci 19, 41-46, https://doi.org/10.1111/j.1744-7917.2011.01447.x (2012).

Rodrigues, T. B., Dhandapani, R. K., Duan, J. J. & Palli, S. R. RNA interference in the Asian Longhorned Beetle: Identification of Key RNAi Genes and Reference Genes for RT-qPCR. Scientific Reports 7, 8913,https://doi.org/10.1038/s41598-017-08813-1 (2017).

Taning, C. N. T., Andrade, E. C., Hunter, W. B., Christiaens, O. & Smagghe, G. Asian Citrus Psyllid RNAi Pathway—RNAi evidence. Scientific Reports 6, https://doi.org/10.1038/srep38082 (2016).

Wang, K. et al. Variation in RNAi efficacy among insect species is attributable to dsRNA degradation in vivo. Insect Biochem Mol Biol 77, 1-9, https://doi.org/10.1016/j.ibmb.2016.07.007 (2016).

Zhao C, Gonzales MAA, Poland TM, Mittapalli O (2015) Core RNAi machinery and gene knockdown in the emerald ash borer (*Agrilus planipennis*). J Insect Physiol 72:70-78. https://doi.org/10.1016/j.jinsphys.2014.12.002.

\* cited by examiner

GENE SILENCING KILLS EMERALD ASH BORER, AN EXOTIC, INVASIVE TREE-KILLING INSECT

RELATED APPLICATIONS

This application claims priority from U.S. Provisional Patent Application No. 62/822,356 filed on Mar. 22, 2019 the entire disclosure of which is incorporated herein by this reference.

GOVERNMENT INTEREST

This invention was made with government support under grant number 2351197000 awarded by the United States Department of Agriculture. The government has certain rights in the invention.

SEQUENCE LISTING

This application contains a sequence listing submitted in accordance with 37 C.F.R. 1.821, named 13177N_2324US RIESKE-KINNEY Sequence Listing.txt, created on Mar. 23, 2020, having a size of 15,445 bytes, which is incorporated herein by this reference

TECHNICAL FIELD

The present disclosure is directed to RNAi-based methods and compositions for pest control of the highly invasive *Agrilus planipennis*.

BACKGROUND

RNA interference (RNAi) is a specific gene-silencing mechanism that is being developed as a tool in pest management programs to protect plants against insect pests. Because its mode of action involves silencing specific target genes based on complementary sequences, RNAi is considered more specific than broad-spectrum and conventional pesticides, decreasing the chances of collateral damage and negative effects on non-target and beneficial organisms[1]. In addition, the diversity of Dicer-substrate siRNAs produced after dsRNA cleavage may impede the evolution of RNAi resistance due to polymorphism in the nucleotide sequences, thereby increasing the durability of RNAi technology in the field. Utilization of RNAi technology to protect agricultural crops is more advanced than in horticultural crops or forestry[3-6].

The efficacy of RNAi varies among insects, and several critical factors may be responsible for the differences observed. The target gene(s) and the level of expression[7-9], the concentration of double-stranded RNA (dsRNA) used[10], combinations of different dsRNAs[11], and delivery methods[12] could affect RNAi efficacy. dsRNAs are delivered through transgenic plants or by topical applications including trunk injection, root absorption, or spraying[2]. Since deployment of genetically engineered trees in reforestation remains contentious[5,13], non-transgenic RNAi methods may be more readily accepted by foresters, land managers, conservationists, and the general public.

RNAi works well in beetles[14,15] and therefore, coleopteran forest pests including the emerald ash borer (*Agrilus planipennis*, EAB) and Asian longhorned beetle (*Anoplophora glabripennis*, ALB) are potential targets for RNAi-mediated control. Both beetles are non-native introductions that have become invasive in North America due to an abundance of highly susceptible host plant material and a lack of effective population regulators[16,17]. Both EAB and ALB have been shown to respond to RNAi, therefore this technology may be feasible for their control[11,18]. Initial work with EAB demonstrated that oral delivery of dsRNA targeting iap (inhibitor of apoptosis) and cop (COPI coatomer, b subunit) genes causes mortality and gene silencing in neonate larvae after 10 days of exposure[11]. However, selection of optimal target gene(s) for a given insect requires extensive screening of multiple dsRNAs, which is typically done via micro-injection. In *Tribolium castaneum*, for instance, a large-scale screen identified 40 most effective genes that caused 50-100% mortality at 8 days post-injection[9]; eleven of those genes caused >80% mortality on day 6, and 100% on day 8 after injection.

Screening target genes for RNAi by microinjection of dsRNA is not an option for EAB neonate larvae because of their small size, delicate form, and their endophagous feeding habits[11]. Additionally, RNAi efficiency varies with delivery method, and dsRNA injection is typically more efficient than dsRNA feeding[19]. Finally, oral dsRNA delivery is essential given that one of the goals is to develop a method for controlling EAB using RNAi technology. First a group of genes were screened by feeding dsRNA to neonate larvae and three target genes that caused the highest mortality were selected. The expression of the three selected genes was evaluated in EAB eggs, larvae, and adults, and knockdown of target genes after dsRNA exposure was determined in larvae and adults. Additionally, the mortality rate after ingestion of individual and combined dsRNAs was evaluated in both larvae and adults. Finally, a non-target organism, *T. castaneum*, was used to evaluate the specificity of the designed EAB dsRNAs.

An embodiment of the present invention is a method of inducing RNAi in an insect from the Coleoptera order comprising administering to the insect about 1 µg/µL to about 20 µg/µL total dsRNA, wherein the total dsRNA includes one or a combination of dsRNAs targeting the genes shibire (SHI) heat shock 70-kDa protein cognate 3 (HSP), and U1 small nuclear ribonucleoprotein (RNP).

A further embodiment of the present invention is a composition comprising about 30-50% by wt sucrose solution, and about 1 µg/µL to about 20 µg/µL total dsRNA, wherein the total dsRNA includes one or a combination of dsRNAs targeting the genes shibire (SHI), heat shock 70-kDa protein cognate 3 (HSP), and U1 small nuclear ribonucleoprotein (RNP).

SUMMARY

The presently-disclosed subject matter meets some or all of the above-identified needs, as will become evident to those of ordinary skill in the art after a study of information provided in this document.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

In some embodiments, the present disclosure is directed to a method of inducing RNAi in an insect of the order Coleoptera, comprising: administering to the insect total dsRNA, wherein the total dsRNA includes one or a combination of dsRNAs targeting the genes shibire (SHI) heat shock 70-kDa protein cognate 3 (HSP), U1 small nuclear ribonucleoprotein (RNP), actin (ACT1), regulatory particle triple-a atpase 3 (RPT3), regulatory particle non-atpase 7 (RPN7), alpha snap (ASNAP), protein phosphatase 1 alpha (PP1A), gawky (GW), inverse regulator a (INRA), and inhibitor of apoptosis (TAP). In further embodiments, the total dsRNA includes a combination of dsRNAs targeting the genes IAP, SHI, HSP, and RNP. In some embodiments, the total dsRNA is administered once daily for 1, 2, 3, 4, 5, 6, 7, or 8 days. In other embodiments, the total dsRNA is administered once daily in an amount of about 1 μg/μL to about 20 μg/μL. In further embodiments, the total dsRNA is administered once daily in an amount of about 1 μg/μL to about 20 μg/μL. In some embodiments the insect is of the Coleoptera order. In other embodiments, the insect is *Agrilus planipennis*. In further embodiments of the present invention, the method does not cause mortality in *Tribolium castaneum, Leptinotarsa decemlineata, Coleomegilla maculate, Apis mellifera, Tetrastichus planipennisi*, or *Spathius galinae*.

In another embodiment, the present invention is directed towards a composition comprising: a sucrose solution; and total dsRNA; wherein total dsRNA includes one or more of dsRNAs targeting the genes shibire (SHI), heat shock 70-kDa protein cognate 3 (HSP), U1 small nuclear ribonucleoprotein (RNP), actin (ACT1), regulatory particle triple-a atpase 3 (RPT3), regulatory particle non-atpase 7 (RPN7), alpha snap (ASNAP), protein phosphatase 1 alpha (PP1A), gawky (GW), inverse regulator a (INRA), and inhibitor of apoptosis (TAP). In further embodiments, the total dsRNA includes a combination of dsRNAs targeting the genes IAP, SHI, HSP and RNP. In other embodiments of the present invention, each dsRNA in a combination of dsRNAs is provided in an equal concentration. In further embodiments, the sucrose solution is in an amount of about 30-50% by wt. In some embodiments, the total dsRNA in an amount of about 1 μg/μL to about 20 μg/μL.

In another embodiment, the present invention relates to a method comprising administering a composition comprising: a sucrose solution; and total dsRNA; wherein total dsRNA includes one or more of dsRNAs targeting the genes shibire (SHI), heat shock 70-kDa protein cognate 3 (HSP), U1 small nuclear ribonucleoprotein (RNP), actin (ACT1), regulatory particle triple-a atpase 3 (RPT3), regulatory particle non-atpase 7 (RPN7), alpha snap (ASNAP), protein phosphatase 1 alpha (PP1A), gawky (GW), inverse regulator a (INRA), and inhibitor of apoptosis (IAP) to an insect.

DESCRIPTION OF EXEMPLARY EMBODIMENTS

Figure 1:
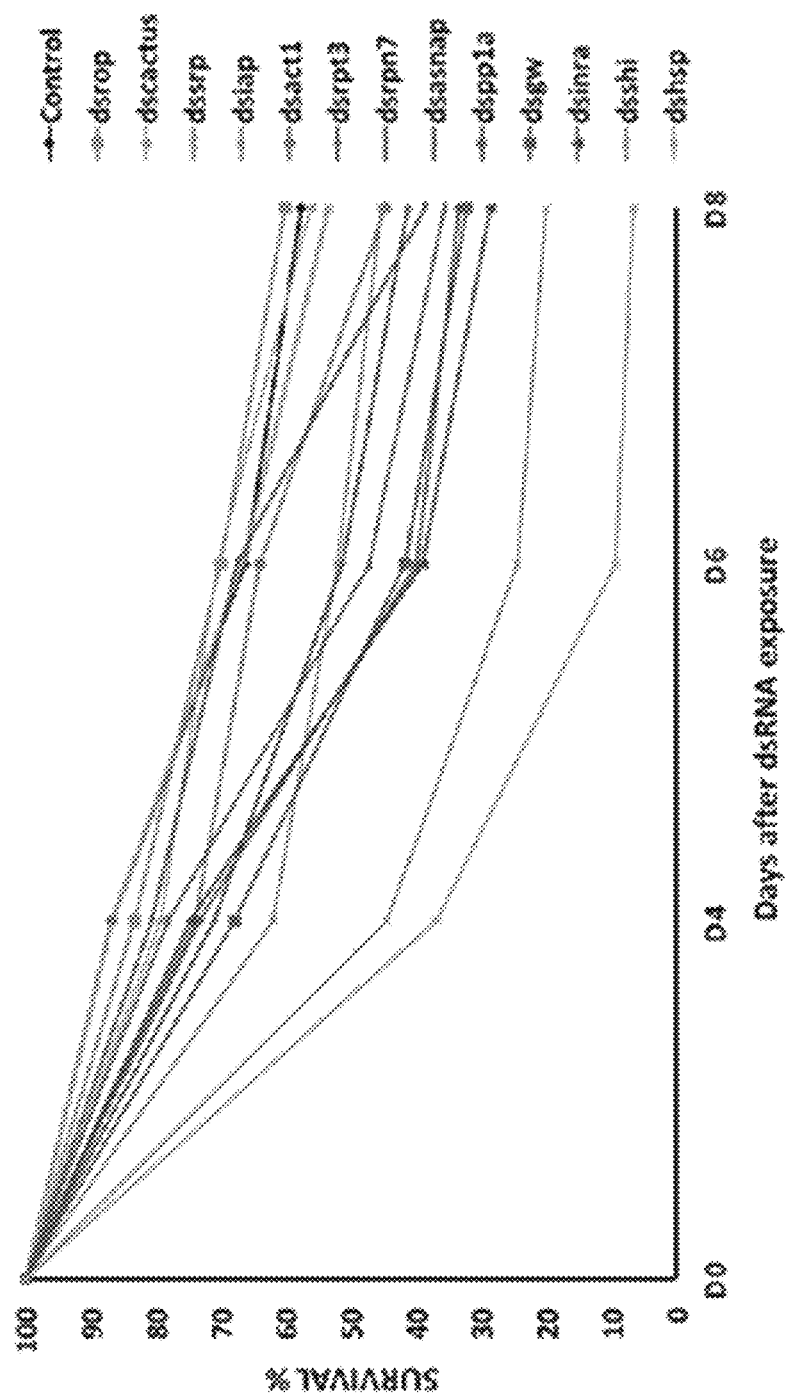
FIG. 1 illustrates screening of dsRNAs in EAB neonate larvae. Using a droplet feeding bioassay, neonate larvae were fed on dsRNAs at 10 μg/μL concentration for 4 d, followed by feeding sucrose solution without dsRNA. After day 4, mortality was recorded every 2 d until day 8. dsIAP was used as a positive control and dsmalE or dsGFP were negative controls. Bioassays were repeated twice for each treatment and 6× for control.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

While the terms used herein are believed to be well understood by those of ordinary skill in the art, certain definitions are set forth to facilitate explanation of the presently-disclosed subject matter.

Unless defined otherwise, all technical and scientific terms used herein have the same meaning as is commonly understood by one of skill in the art to which the invention(s) belong.

All patents, patent applications, published applications and publications, GenBank sequences, databases, websites and other published materials referred to throughout the entire disclosure herein, unless noted otherwise, are incorporated by reference in their entirety.

Where reference is made to a URL or other such identifier or address, it understood that such identifiers can change and particular information on the internet can come and go, but equivalent information can be found by searching the internet. Reference thereto evidences the availability and public dissemination of such information.

As used herein, the abbreviations for any protective groups, amino acids and other compounds, are, unless indicated otherwise, in accord with their common usage, recognized abbreviations, or the IUPAC-IUB Commission on Biochemical Nomenclature (see, Biochem. (1972) 11(9): 1726-1732).

Although any methods, devices, and materials similar or equivalent to those described herein can be used in the practice or testing of the presently-disclosed subject matter, representative methods, devices, and materials are described herein.

Following long-standing patent law convention, the terms "a", "an", and "the" refer to "one or more" when used in this application, including the claims. Thus, for example, reference to "a biomarker" includes a plurality of such biomarkers, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, width, length, height, concentration or percentage is meant to encompass variations of in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, "optional" or "optionally" means that the subsequently described event or circumstance does or does not occur and that the description includes instances where said event or circumstance occurs and instances where it does not. For example, an optionally variant portion means that the portion is variant or non-variant.

As used herein, the term "subject" refers to a target of administration. The subject of the herein disclosed methods can be an insect. Thus, the subject of the herein disclosed methods can include an insect of the order Coleoptera and the genus *Agrilus*. The term does not denote a particular age or sex.

As used herein, the terms "administering" and "administration" refer to any method of providing a pharmaceutical preparation to a subject. Such methods are well known to those skilled in the art and include, but are not limited to, oral administration, dermal administration via the cuticle, ophthalmic administration, intracerebral administration, and respiratory administration, and injectable administration. Administration can be continuous or intermittent.

As used herein, the term "effective amount" refers to an amount that is sufficient to achieve the desired result or to have an effect on an undesired condition. For example, a "effective amount" may refer to an amount that is sufficient to achieve the desired therapeutic result or to have an effect on undesired outcomes, but is generally insufficient to cause adverse side effects. For example, it is undesirable in the instant invention to have effects on certain native species such as *Tribolium castaneum, Leptinotarsa decemlineata, Coleomegilla maculate, Apis mellifera, Tetrastichus planipennisi,* or *Spathius galinae.*

The presently-disclosed subject matter is further illustrated by the following specific but non-limiting examples. The following examples may include compilations of data that are representative of data gathered at various times during the course of development and experimentation related to the present invention.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

The presently-disclosed subject matter is further illustrated by the following specific but non-limiting examples. The following examples may include prophetic examples, notwithstanding the numerical values, results and/or data referred to and contained in the examples. The following examples may include compilations of data that are representative of data gathered at various times during the course of development and experimentation related to the present invention.

EXAMPLES

Example 1

Results

Figures 2A, 2B:
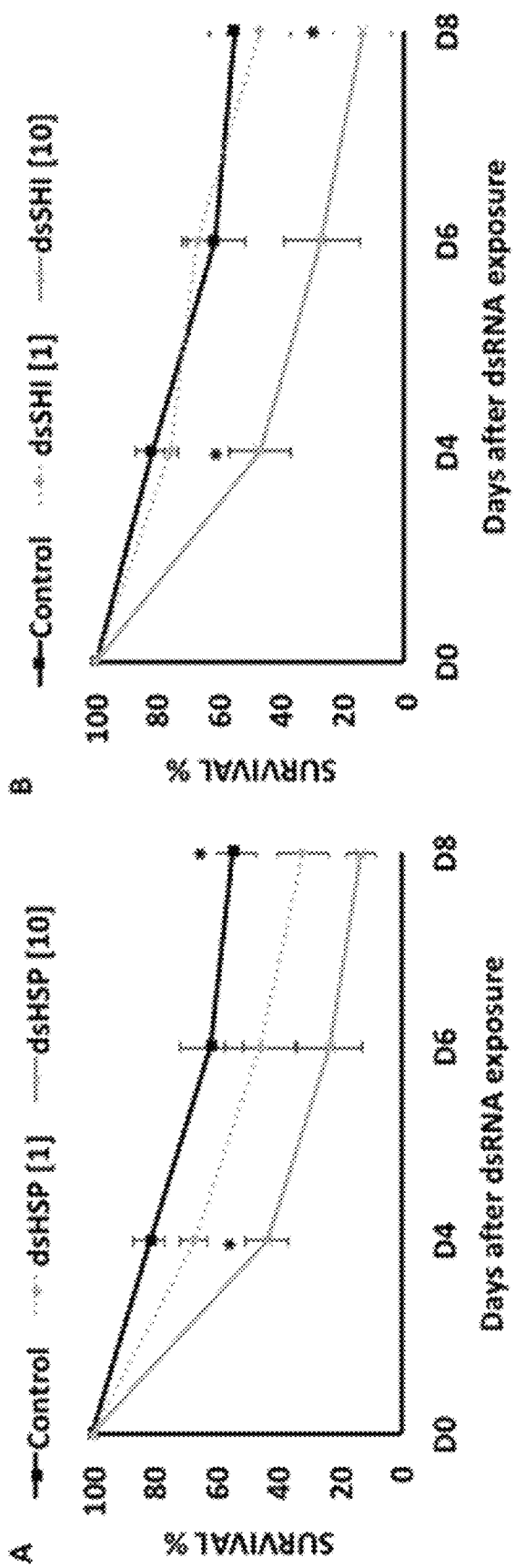
FIG. 2A depicts how EAB survival is evaluated after 8 d of feeding on dsRNA. (A) Neonate larvae were fed on two different concentrations of dsHSP for 4 days. Control=dsmalE or dsGFP at a concentration of 10 μg/μL (N=6); dsHSP [1]=1 μg/μL (N=4); dsHSP [10]=10 (N=3). P=0.002.
FIG. 2B Neonate larvae were fed on two different concentrations of dsSHI for 4 days. dsmalE or dsGFP at a concentration of 10 μg/μL (N=6) were used as control. dsSHI [1]=1 μg/μL (N=3); dsSHI [10]=10 μg/μL (N=4). The asterisk reflects significantly different mortality rate (ANOVA, Student-Newman-Keuls, P=0.01).

Screening of candidate genes. The mortality of neonate larvae following ingestion of dsRNA varied among the genes tested with most causing 13 to 38% mortality (FIG. 1). After 4 d of dsRNA exposure, 13.2% mortality was recorded in negative controls (dsGFP and dsMalE), and 38% mortality in the positive control (dsIAP). However, ingestion of dsRNA targeting shi and hsp caused 55.5 and 63% mortality after 4 d, and reached 80 and 93.3% mortality, respectively, after 8 d of dsRNA exposure. Among the 13 genes targeted, ingestion of dsSHI and dsHSP was most effective in EAB neonates, causing the highest mortality following dsRNA exposure.

dsRNA dosage response. The two genes that caused the highest mortality, hsp and shi, were selected for further experiments to determine optimum dsRNA doses. Neonate larvae were fed on high (10 mg/mL of dsHSP or dsSHI) and low (1 mg/mL of dsHSP or dsSHI) doses of dsRNA. Neonates that ingested the high dose of either dsRNA experienced 90% mortality, whereas those that ingested low doses of dsHSP experienced 67% mortality after 8 d (FIG. 2A). In contrast, mortality of neonates ingesting 1 mg/mL of dsSHI did not differ from the control (FIG. 2B).

Figures 3A, 3B, 3C:
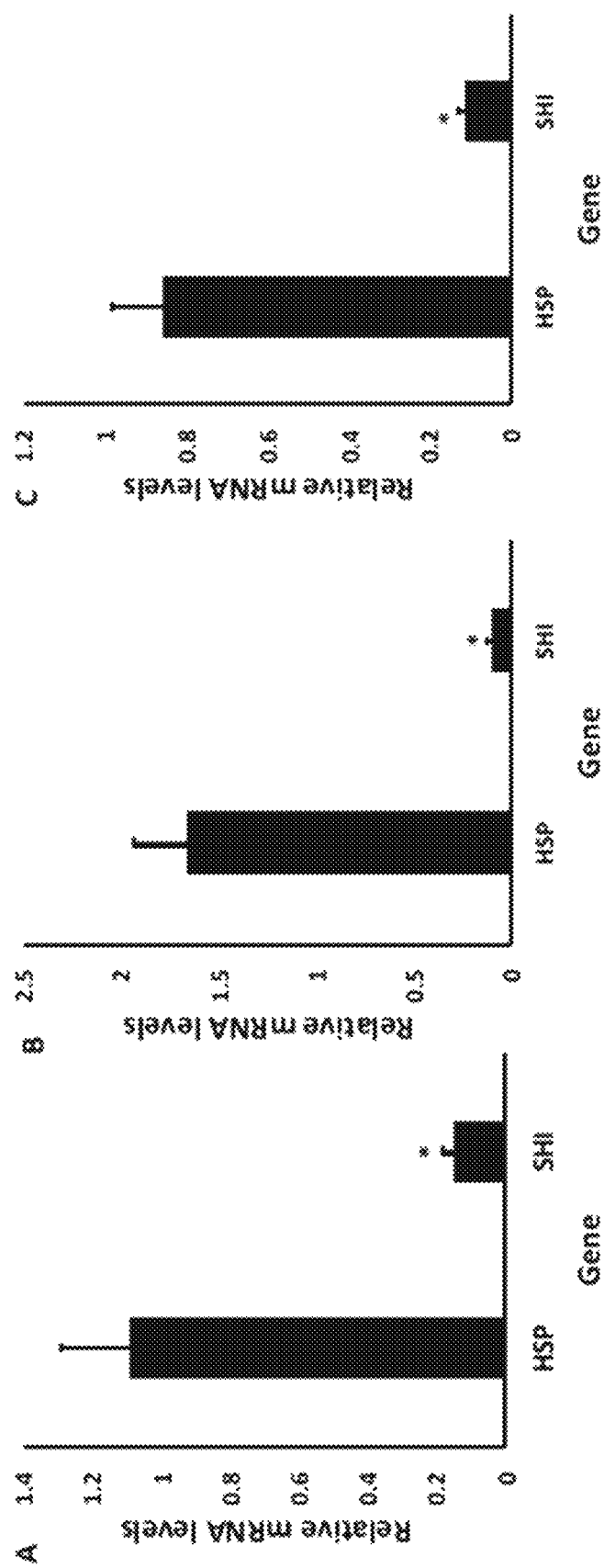
FIG. 3A shows the relative expression of hsp and shi genes in EAB eggs, were exposed to dsGFP (control) and total RNA isolated after 48 h. Relative mRNA levels were normalized using TEF as a reference gene. Mean+S.E are shown. The asterisk denotes significant differences (t-test, two-tailed P-value: P=0.002 (A).
FIG. 3B shows the relative expression of hsp and shi genes in EAB neonate larvae were exposed to dsGFP (control) and total RNA isolated after 72 h Relative mRNA levels were normalized using TEF as a reference gene. Mean+S.E N=3. The asterisk denotes significant differences. P=0.009.
FIG. 3C shows the relative expression of hsp and shi genes in EAB adults were exposed to dsGFP (control) and total RNA isolated after 24 h Relative mRNA levels were normalized using TEF as a reference gene. Mean+S.E N=5. The asterisk denotes significant differences P=0.002.

Gene expression. The relative expressions of hsp and shi genes were compared in EAB eggs, larvae, and adults (FIG. 3A-3C). In all life stages tested, hsp gene expression is >8× more than shi gene expression.

Figure 4:
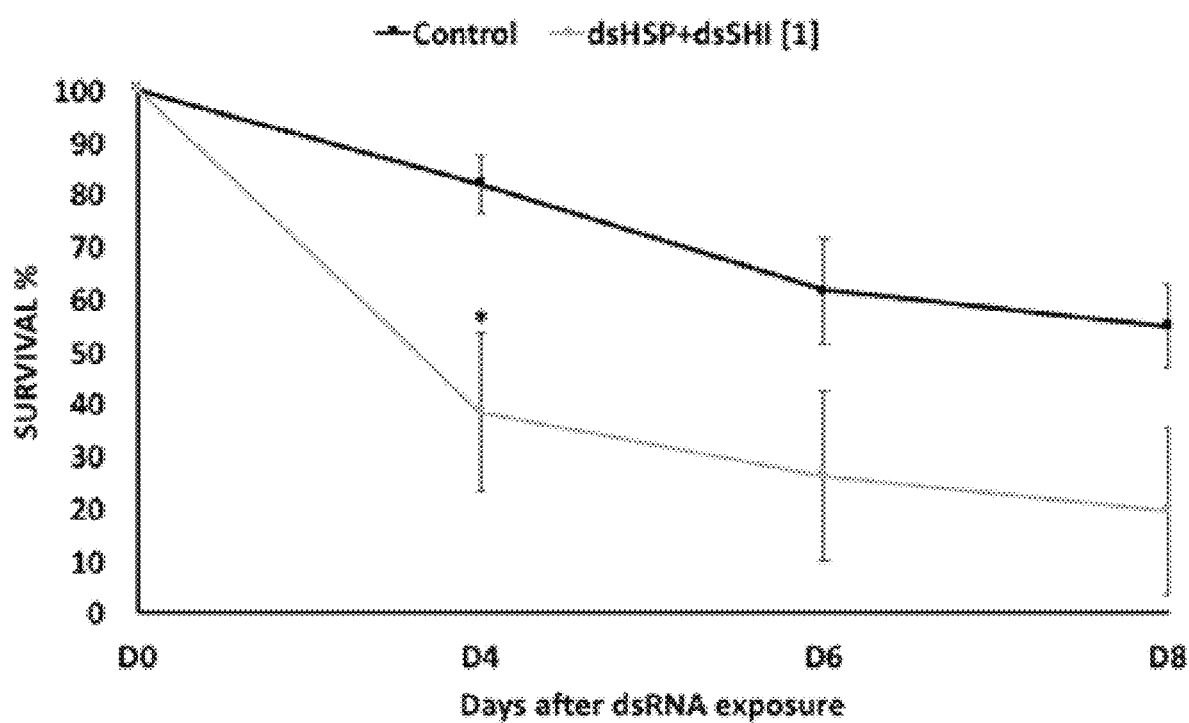
FIG. 4 depicts larval EAB survival after 8 days fed on a combination of dsRNAs. Neonates were exposed to 1 μg/μL of dsRNA (500 ng/μL each dsHSP and dsSHI; N=3) for 4 consecutive days and then fed on blue-sucrose solution without dsRNA until day 8; 10 μg/μL of dsmalE or dsGFP (N=6) were used as control. The asterisk denotes days of exposure when treatments are significantly different (t-test, two-tailed P-value: P=0.007).

Combination of dsRNA. Neonate larvae fed on 1 µg/µL of both dsHSP and dsSHI (500 ng/µL of each) for 4 d had higher mortality after 4, 6, and 8 d (61.6%, 73.8%, and 80.5%, respectively; FIG. 4) than the larvae fed on 1 µg/µL of dsHSP (FIG. 2A) or 1 µg/µL of dsSHI (FIG. 2B).

Figure 5B:
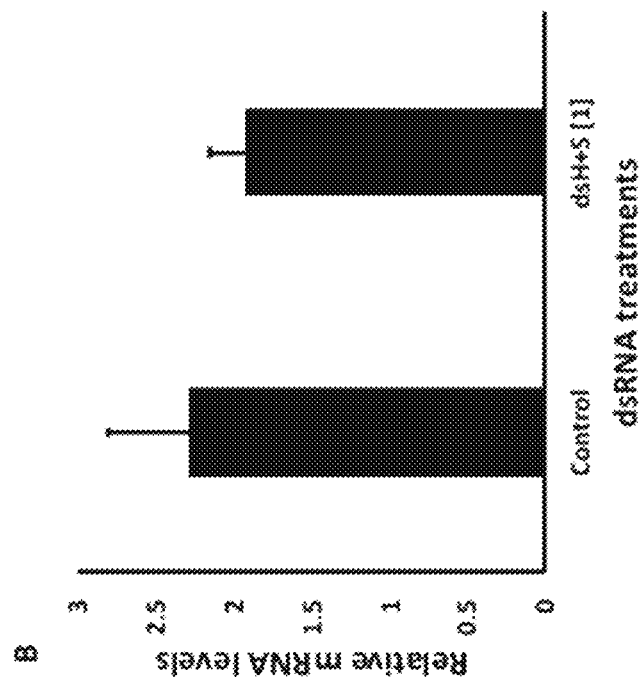
FIG. 5B shows relative expression of shi genes in EAB larvae after 3 days feeding on 1 μg/μL of combined dsRNAs (500 ng/μL each dsHSP and dsSHI); 10 μg/μL of dsGFP was used as control. Relative mRNA levels were normalized using TEF as a reference gene. Mean+S.E (N=3) are shown. The asterisk above the bar indicates significantly different expression (t-test, two-tailed P-value: P=0.635.
Figure 5A:
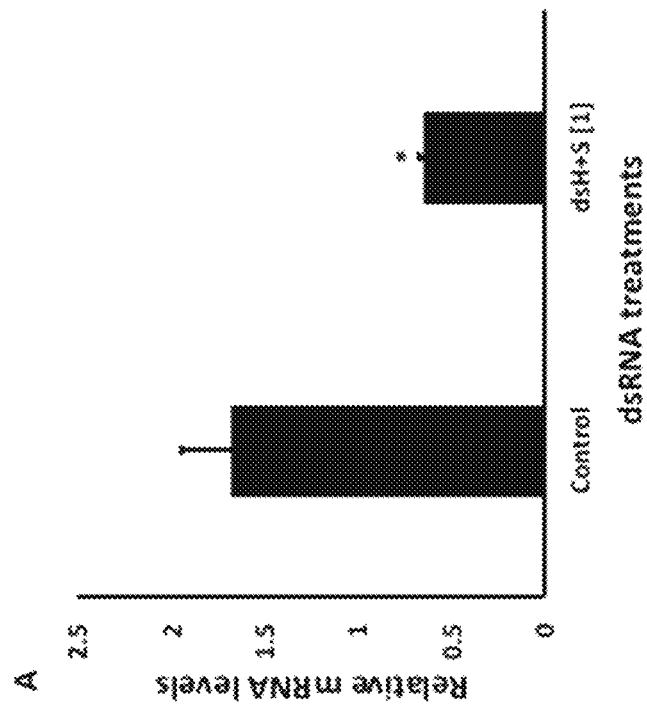
FIG. 5A shows relative expression of hsp genes in EAB larvae after 3 days feeding on 1 μg/μL of combined dsRNAs (500 ng/μL each dsHSP and dsSHI); 10 μg/μL of dsGFP was used as control. Relative mRNA levels were normalized using TEF as a reference gene. Mean+S.E (N=3) are shown. The asterisk above the bar indicates significantly different expression (t-test, two-tailed P-value: P=0.038.
Figure 6A:
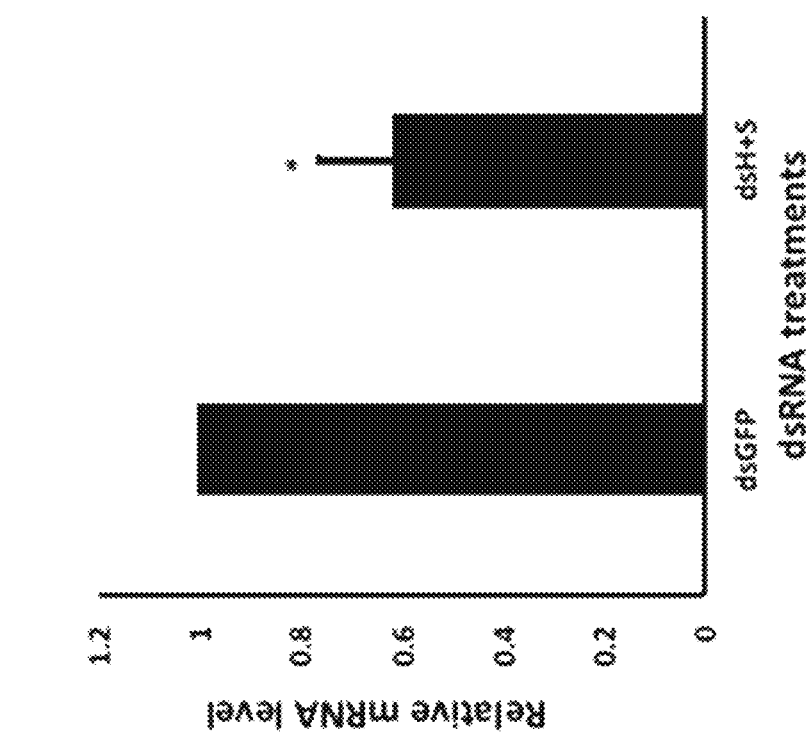
FIG. 6A shows relative expression of hsp genes in EAB adults 24 h after injection of 20 μg/μL of dsRNA (10 μg/μL each dsHSP and dsSHI); 20 μg/μL of dsGFP were used as control. Relative mRNA levels were normalized using TEF as a reference gene. Mean+S.E (N=5) are shown (t-test, two-tailed P-value: P=0.05.
Figure 6B:
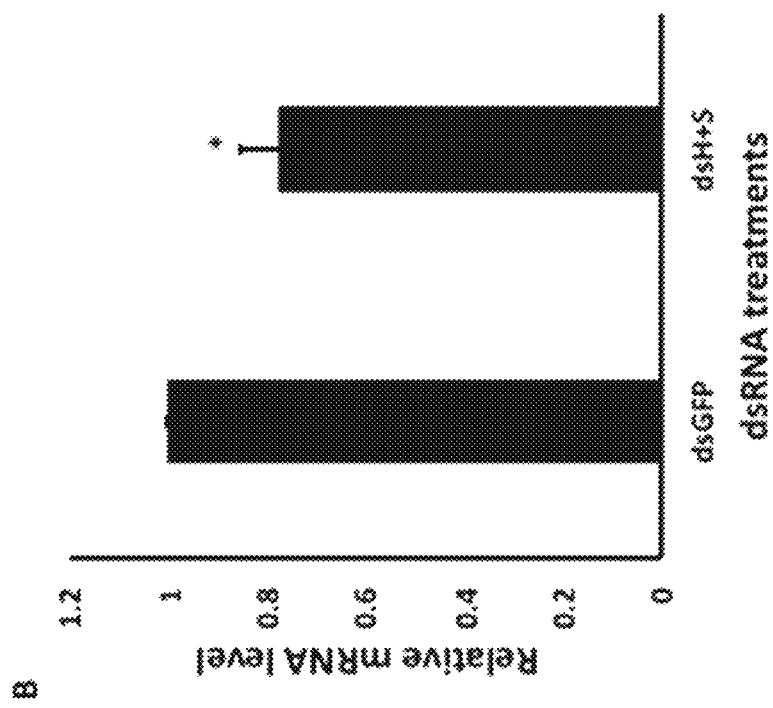
FIG. 6B shows relative expression of shi genes in EAB adults 24 h after injection of 20 μg/μL of dsRNA (10 μg/μL each dsHSP and dsSHI); 20 μg/μL of dsGFP were used as control. Relative mRNA levels were normalized using TEF as a reference gene. Mean+S.E (N=5) are shown (t-test, two-tailed P-value: P=0.02.

Gene silencing. Neonates fed on 1 µg/µL of both dsHSP and dsSHI (500 ng/µL of each) for 3 d showed a decrease in the mRNA levels of hsp (62%) and shi (15%) when compared to their levels in neonates that fed on dsGFP (FIG. 5A,B). In adults, injection of 20 µg/µL of both dsHSP and dsSHI (10 µg/µL of each) resulted in 20-40% silencing ($p<0.05$) of both hsp and shi genes at 24 h after injection (FIG. 6A,6B).

Figure 7:
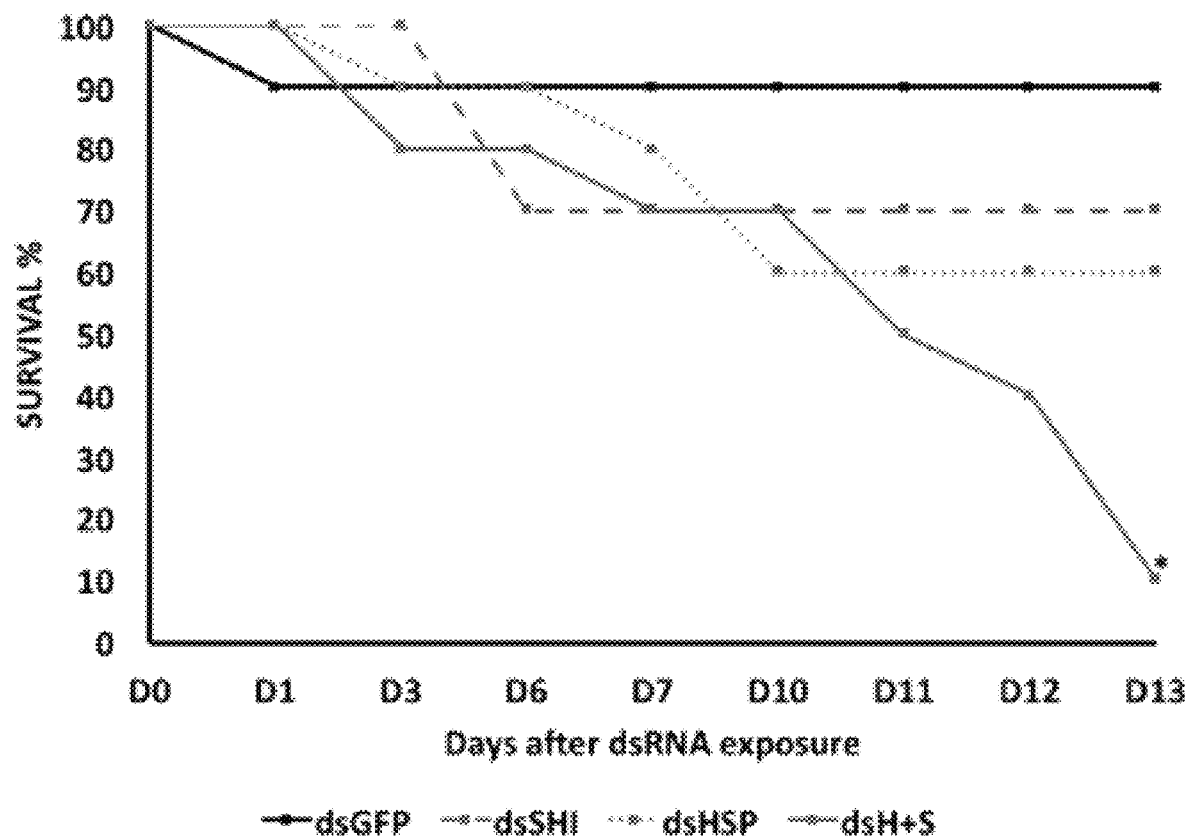
FIG. 7 shows adult EAB survival at 14 days after feeding on 2 μL of dsRNA at a final concentration of 10 μg/μL of single dsGFP (control), single dsHSP, and single dsSHI and 1 μg/μL of combined dsHSP and dsSHI (500 ng/μL of each). The asterisk indicates significant differences in mortality between treatment and control (Fisher's Exact test, two-tailed, P-value=0.011, N=10).

Adult mortality. In the adult feeding trial, beetles were fed on 10 µg/µL dsSHI, 10 dsHSP, 1 dsHSP+dsSHI (500 ng/µL of each), or a 10 µg/µL dsGFP control. There were no effects detected on day 1 with the exception of a single beetle lost in the control treatment, which then remained constant through day 13. Adult beetles fed on dsSHI experienced 30% mortality at 6 d, which persisted through the experiment. Adult mortality became evident at 3 d in adults fed on dsHSP (10%); mortality rose to 40% for dsHSP-exposed beetles for the duration of the experiment. However, for beetles fed on 1 µg/µL of combined dsHSP and dsSHI, 90% mortality was evident on day 13 (FIG. 7).

TABLE 1

| Gene Name | T. castaneum Accession | Query Cover | E-value | Identity | Mortality* (10 dai) |
|---|---|---|---|---|---|
| shi | XM_008200600.2 | 92% | 3e−49 | 91% | 0% |
| hsp | XM_015982882.1 | 78% | 7e−29 | 85% | 0% |

EAB.dsRNA in *Tribolium castaneum.*

The nucleic acid sequences of the EAB hsp and shi showed 85% and 91% identity, respectively, with the homologues in *T. castaneum.* Injection of EAB dsHSP and dsSHI into *T. castaneum* adults caused no mortality (Table 1). Table 1 shows Similarity between *A. planipennis* dsRNA designed sequences and *T. castaneum* genes. dai: days after dsRNA injection. *Sun-Shepard's formula was used to adjust for mortality.

Methods

Insects.

Laboratory-reared *A. planipennis* eggs were placed in Petri dishes (150, 15 mm) with moistened filter paper and maintained at 23° C. and 75% relative humidity in a growth chamber. Newly hatched unfed neonate larvae at <48 h post-hatch were used in bioassays. Adults were reared in the laboratory at 23° C. from field-collected green ash (*F. pennsylvanica*), and maintained on either green or tropical ash (*F. uhdei*) foliage.

TABLE 2

| Gene Name | Primer name-dsRNA size | Primer Sequence | Ap sequence ID |
|---|---|---|---|
| srp54k | ds - EAB srp - 496 bp - F | TAATACGACTCACTATAGGGGG CTGTAGCAAATGCAGTGA (SEQ ID NO: 1) | XM_018478973.1 |

TABLE 2-continued

| Gene Name | Primer name-dsRNA size | Primer Sequence | Ap sequence ID |
|---|---|---|---|
| | ds - EAB srp - 496 bp - R | TAATACGACTCACTATAGGGAC GCGCCATAGACTCTTGTT (SEQ ID NO: 2) | |
| ras opposite | ds - EAB rop - 493 bp - F | TAATACGACTCACTATAGGGGC CGACACCTTTCAGTGTTT (SEQ ID NO: 3) | XM_018464595.1 |
| | ds - EAB rop - 493 bp - R | TAATACGACTCACTATAGGGGCT TGGAATCGGTGAACTTT (SEQ ID NO: 4) | |
| shibire | ds - EAB shi - 483 bp - F | TAATACGACTCACTATAGGGTG GCACATTTGTATGCCAGT (SEQ ID NO: 5) | XM_018465318.1 |
| | ds - EAB shi - 483 bp - R | TAATACGACTCACTATAGGGCTT GTTGCATTTGCTGAGGA (SEQ ID NO: 6) | |
| protein phosphatase 1 alpha at 96a | ds - EAB pp1a - 532 bp - F | TAATACGACTCACTATAGGGTAT GTGTACGTGTGCCCGTT (SEQ ID NO: 7) | XM_018468028.1 |
| | ds - EAB pp1a - 532 bp - R | TAATACGACTCACTATAGGGTTG ATGAAGAGCAAGCGAAA (SEQ ID NO: 8) | |
| regulatory particle non-atpase 7 | ds - EAB rpn7 - bp - F | TAATACGACTCACTATAGGGTTG AAGAGGGAGGTGATTGG (SEQ ID NO: 9) | XM_018468408.1 |
| | ds - EAB rpn7 - bp - R | TAATACGACTCACTATAGGGTG ATCCGGCCTATTTGTCTC (SEQ ID NO: 10) | |
| regulatory particle triple-a atpase 3 | ds - EAB rpt3 - 513 bp - F | TAATACGACTCACTATAGGGGC CAAAGCAGTAGCACATCA (SEQ ID NO: 11) | XM_018479000.1 |
| | ds - EAB rpt3 - 513 bp - R | TAATACGACTCACTATAGGGAG CATGCATTCCAGCTTCTT (SEQ ID NO: 12) | |
| actin | ds - EAB act1 - 427 bp - F | TAATACGACTCACTATAGGGGCT AACCGCGAGAAGATGAC (SEQ ID NO: 13) | XM_018481271.1 |
| | ds - EAB act1 - 427 bp - R | TAATACGACTCACTATAGGGGG AACCTTTCGTTTCCAACA (SEQ ID NO: 14) | |
| cactus | ds - EAB cact - 389 bp - F | TAATACGACTCACTATAGGGAT GTTGTGTTGGTGCGAAAA (SEQ ID NO: 15) | XM_018478973.1 |
| | ds - EAB cact - 389 bp - R | TAATACGACTCACTATAGGGTTC CCGAACTAAGGTCGTTG (SEQ ID NO: 16) | |
| alpha snap | ds - EAB asnap - 484 bp - F | TAATACGACTCACTATAGGGGT AGTGCATTTTGCGAAGCA (SEQ ID NO: 17) | XM_018465131.1 |
| | ds - EAB asnap - 484 bp - R | TAATACGACTCACTATAGGGTG ACGAGCATTCAGCAAATC (SEQ ID NO: 18) | |
| inverse regulator a | ds - EAB inra - 449 bp - F | TAATACGACTCACTATAGGGAC CGGTGTTACCAAAGCAAG (SEQ ID NO: 19) | XM_018464445.1 |
| | ds - EAB inra - 449 bp - R | TAATACGACTCACTATAGGGGC GCTATTAACAGGCGCTAC (SEQ ID NO: 20) | |

TABLE 2-continued

| Gene Name | Primer name-dsRNA size | Primer Sequence | Ap sequence ID |
|---|---|---|---|
| heat shock 70-kDa protein cognate 3 | ds - EAB hsc70-3 - 468 bp - F | TAATACGACTCACTATAGGGGTT ACGAGCCAGGGTGAAAA (SEQ ID NO: 21) | XM_018474521.1 |
| | ds - EAB hsc70-3 - 468 bp - R | TAATACGACTCACTATAGGGCTT TTGAACGGCACGGTTAT (SEQ ID NO: 22) | |
| gawky | ds - EAB gw - 442 bp - F | TAATACGACTCACTATAGGGCA ACATTGCGCCGACTACTA (SEQ ID NO: 23) | XM_018475118.1 |
| | ds - EAB gw - 442 bp - R | TAATACGACTCACTATAGGGCC ACATTCCTCCTCCACTGT ((SEQ ID NO: 24) | |

Selection of Target Genes and Synthesis of dsRNA.

PCR templates for in vitro transcription of dsRNA were generated using gene-specific primers containing T7 polymerase promoter sequence (TAATACGACTCACTATAGGG) (SEQ ID NO: 25) at the 5' end (Table 2). Table 2 shows primer sequence, dsRNA size and NCBI sequence ID for the target genes. All primers contain the promoter sequence of T7 RNA Polymerase that is represented in the table. Candidate genes were selected based on previous reports of mortality in *T. castaneum* exposed to dsRNAs targeting these genes[9]. PCR conditions were 94° C. for 4 min, followed by 35 cycles of 94° C. for 30 s, 60° C. for 30 s and 72° C. for 45 s, finishing with an extension step at 72° C. for 10 min. The PCR template was purified using a PCR purification kit (Qiagen Inc., Valencia, Calif. USA). As a negative control, a fragment of GFP (green fluorescence protein) was used. After PCR purification, dsRNA synthesis was performed using the MEGAscript RNAi Kit (Ambion Inc., Foster City, Calif. USA) following manufacturer's instructions. Briefly, 200 ng of purified PCR product was used as template in a 20 mL in vitro transcription reaction. The reaction was incubated for 16 h at 37° C., followed by 15 min of DNase treatment. The dsRNA was precipitated by adding 0.1× volume of sodium acetate (3 M, pH 5.2) and 2.5× the volume of 100% ethanol; kept at −20° C. for at least 2 h followed by centrifugation at 4° C. for 30 min. The dsRNA pellet was then rinsed with 750 mL of 75% ethanol and centrifuged again at 4° C. for 15 min. The ethanol was removed and the dsRNA was diluted in ultrapure distilled water. The quality of the dsRNA was checked by electrophoresis and quantified using a spectrophotometer (Nano-Drop Technologies, Wilmington, Del. USA). When a higher concentration of dsRNA was needed, the samples were vacuum concentrated using Concentrator plus (Eppendorf, Hauppauge, N.Y., USA).

Screening Assays.

A droplet bioassay[11] was used to screen potential target genes for EAB suppression. Twelve candidate genes (Table 2) and positive and negative controls were evaluated. Inhibitor of apoptosis gene (iap 1), previously shown to cause mortality after dsIAP exposure in both EAB and ALB[11,18], was used as a positive control, and green fluorescent protein (gfp) was used as a negative control. Droplets of dsRNA (2 ml each) at a concentration of 10 mg/ml diluted in blue sucrose solution were used to feed 3-4 neonate EAB larvae in covered petri dishes with moistened filter paper. The blue dye in the sucrose-dsRNA solution allowed us to confirm neonate larval consumption. Neonates were exposed to dsRNA for 4 consecutive days; droplets were replenished on the rare occasions when the solution was completely consumed or evaporated. On day 5, larvae were transferred to new plates containing droplets of sucrose solution without dsRNA. Larval mortality was recorded at 48 h intervals through day 8 after dsRNA feeding treatment. Experiments were repeated twice under the same conditions using 20 neonate larvae per treatment. If the two repeats showed variability, a third repeat was performed. The dsRNAs that showed higher mortality after 8 d were repeated at least one more time, for a total of three repeats; those with the highest EAB mortality were selected for further experiments to confirm their potential for use in managing EAB.

Dosage Response.

Two concentrations, 1 µg/µL and 10 µg/µL, of dsHSP (targeting heat shock 70-kDa protein cognate 3 gene) and dsSHI (targeting shibire gene) were used to evaluate neonate mortality, and 10 µg/µL dsGFP was used as a control. Larvae were fed on dsRNA for 4 d, followed by 4 d on blue sucrose solution without dsRNA. Mortality (%) was then calculated based on the initial number of larvae (15-20) on day one. The experiment was repeated 3-6 times, and a one-way analysis of variance (ANOVA) was used with Student-Newman-Keuls to evaluate significance of differences.

Combinations of dsRNA.

The two selected dsRNAs, dsHSP and dsSHI, were combined to evaluate larval mortality and gene silencing using the droplet assay. The dsRNAs were diluted in sucrose solution to a final concentration of 10× lower single dsRNA (1 µg/µL dsSHI+dsHSP: 0.5 µg/µL of dsSHI and 0.5 µg/µL of dsHSP). The dsGFP at a concentration of 10 µg/µL was used as a control. Four biological replicates, with 15-20 neonate larvae per replicate, were used and a one-way ANOVA was used for data analysis, with Student-Newman-Keuls to detect significance of differences.

Gene Expression.

Both hsp and shi genes were analyzed for gene expression patterns in eggs, larvae, and adults, and for knockdown after dsRNA exposure in neonate larvae and adults, using dsGFP as a control. For gene expression patterns, the control treatment in neonate larvae and adults was used for the analyses. The eggs were treated with 1 µg/µL of dsGFP followed by a 1 µL droplet of dsRNA (3 times during 48 h). Eggs were maintained at 28° C. for 48 h, and each treatment was performed in triplicate with 6-7 eggs per replicate. For gene knockdown analyses, neonate larvae were fed on both dsSHI and dsHSP (1 µg/µL total, 0.5 µg/µL of each dsRNA) for 72 h; 10 µg/µL of dsGFP was used as a control. Larval assays were performed in triplicate with 6-8 neonates per replicate. Adult beetles were evaluated for hsp and shi gene silencing 24 h after injection with 2 µL of both dsRNAs (dsSHI and dsHSP at 20 µg/insect total, 10 µg/µL of each dsRNA), using dsGFP (20 µg/insect) as a control. Microinjection of dsRNA was chosen because it is faster, easier, and requires fewer insects to perform. Five biological replicates were performed using one beetle in each replicate. Following assays, eggs and neonate larvae were pooled for RNA extraction. RNA was also isolated from each adult beetle. A two-tailed t-test was used for statistical analysis to compare the means of a single variable.

TABLE 3

| Primer Name | Primer Sequence (5'- 3') | Amplicon (bp) |
| --- | --- | --- |
| q- EAB shi - 122 bp - F | GGGATCTGCCCAAATTAACA (SEQ ID NO: 26) | 122 |
| q - EAB shi - 122 bp - R | CCCGTCTGAGTTCTTTCTCG (SEQ ID NO: 27) | |
| q- EAB hsp70-3 -97 bp - F | GACAAAGGAACGGGAAACAA (SEQ ID NO: 28) | 97 |
| q - EAB hsp70-3 -97 bp - R | TCTCGGCATCCCTTATCATC (SEQ ID NO: 29) | |

RT-qPCR.

Total RNA was isolated from 6-10 EAB larvae pooled after feeding on dsRNA using the TRI Reagent RT (Molecular Research Center Inc., Cincinnati, Ohio, USA). The cDNA was synthesized using M-MLV Reverse Transcriptase (Life Technologies, Carlsbad, Calif., USA) from RNA and used as a template for gene expression studies. The expression analyses of the target genes were conducted using SYBR Green PCR Master Mix. Briefly, the PCR mixture contained 1 μL of synthesized cDNA, 0.2 μL of each primer (10 mM; Table 3), 5 μL of the SYBR green PCR master mix and 3.6 μL of ddH$_2$O. Table 3 shows primer sequence and amplicon size for the target genes shi and hsp, for qPCR. The reactions were carried out in duplicate per template in a final volume of 10 μL. RT-qPCR reactions were performed by the StepOnePlus Real-Time PCR system (Life Technologies, Carlsbad, Calif., USA) using the following cycling conditions: one cycle at 95° C. (20 s), followed by 40 cycles of denaturation at 95° C. (3 s), annealing and extension at 60° C. for 30 s. At the end of each RT-qPCR reaction, a melting curve was generated to confirm a single peak and rule out the possibility of primer-dimer and non-specific product formation. The TEF1A was used as reference gene[28], and $-2^{\Delta\Delta Ct}$ method was used to calculate the relative expression levels of the target gene in the samples compared to controls[29]. Standard curves were performed for all the new primers and the correlation coefficients and amplification efficiency parameters were analyzed. A two-tailed t-test was used for statistical analysis to compare the means of a single variable.

Adult Mortality.

A feeding assay was performed to deliver dsRNAs to EAB adults to evaluate the effects of silencing hsp and shi genes. The dsRNAs were diluted with 40% sucrose solution, and each beetle was fed on ~2 μL droplet of the diluted solution of each dsRNA sample. Beetles were fed 10 μL of each dsRNA (dsGFP, dsHSP, and dsSHI), and 1 μL of the combination of dsHSP and dsSHI (500 ng of each). In each treatment, 5 male and 5 female beetles (N=10) were evaluated. Mortality was recorded at 24-48 h intervals for 13 d. After the single dsRNA feeding exposure at day 0, adult beetles were provided with fresh tropical ash foliage and were kept in an environmental chamber (Percival Scientific, Perry, Iowa) at 25+1.5° C., 55-65% RH, and a photoperiod of 16:8 (L:D) h. For data analysis, males and females were combined, and Fisher's test was used to identify statistical differences between treatments.

EAB dsRNA sequences. The sequences listed in Table 4 are example dsRNAs sequences used in the instant invention.

TABLE 4

Sequences of dsRNA for EAB

| Gene target | dsRNA sequence (subsequence of mRNA target) |
| --- | --- |
| srp54k | GGCTGTAGCAAATGCAGTGAAACCTGATAATATTATTTTTGTTATGGAT GCTACAATTGGACAGGCTTGTGAAGCTCAGGCAAAAGCATTTAAAGAA AAGGTTGATGTAGGCTCCGTGATTATAACGAAATTAGATGGCCACGCTA AAGGTGGAGGAGCCCTAAGTGCGGTTGCAGCGACGCAAAGTCCTATAA TTTTTATTGGTACTGGAGAGCACATAGATGACTTAGAACCATTTAAAAC AAAACCATTTATTAGCAAATTACTTGGAATGGGAGATATTGAAGGGTTG ATAGACAAAGTCAATGAATTAAAATTAGAGGACAATGAAGAACTTTTA GAAAAGATCAAACATGGACAGTTTACGCTAAGGGACATGTATGAACAG TTCCAAAATATCATGAAAATGGGTCCTTTTTCACAAATAATGGGGATGA TACCCGGTTTTAGTCAAAGTTTTATGTCAAAAGGTAGTGAACAAGAGTC TATGGCGCGT (SEQ ID NO: 30) |
| ras opposite | GCCGACACCTTTCAGTGTTTTTATGATCCTTCATTTTCTGCTGCAAGAAC TGCCAATATGGAGCGTATGGCCGAACAGATTGCAACCCTCTGTGCTACT CTCGGGGAATACCCTTCAGTGCGCTATAGAGCGGATTGGGACAAAAATG TAGAATTAGCACAGTTAATCCAACAAAAACTAGACGCTTATAAAGCGG ATGAACCGACAATGGGTGAAGGACCGGAAAAAGCTCGTTCACAACTCT TAATTTTGGACAGAGGGTTCGATTGTGTATCGCCTCTCTTACATGAATTA ACATTCCAGGCAATGGCTTACGATTTATTACCAATCGAAAACGACGTAT ATCGCTATGAAGCTACGGCGGGATCGGCTGAAAAGAAGGAAGTTTTGCT TGACGAAAACGACGAATTGTGGGTAGAATTGCGTCATCAGCACATCGCC GTCGTTTCTCAAAGTGTTACCAAAAATTTGAAAAAGTTCACCGATTCCA AGC (SEQ ID NO: 31) |

TABLE 4-continued

Sequences of dsRNA for EAB

| Gene target | dsRNA sequence (subsequence of mRNA target) |
| --- | --- |
| shilbire | TGGCACATTTGTATGCCAGTGGTGATCAGCAACAAATGATGGAAGAATC<br>ACCTGAGGAAGCCTTGAAGCGTGAAGAAATGTTGCGAATGTACCACGC<br>ATGTAAAGAAGCTTTAAGAATAATAGGAGATGTTTCAATGGCTACAGTA<br>TCCACACCGGTACCTCCCCCCGTAAAGAATGACTGGCTGGCAAGCGGCT<br>TGGATAATGCACGATTATCACCACCTAGTCCGGGCGGGAGTAAACGACA<br>GGCTCCGTTAATGAGTCAAGTTGGTTCATCGGGATCGTTAGGTTCTTCCG<br>GCAACGTCAGGGCTCCACCGTTGCCTCCAGCTTCAGGAAGACCGGCTCC<br>TGCGATACCTAATCGACCTGGTGGAGGAATGCCTCCCATGCCACCTGGC<br>AGACCTCAAGGACAACCTCTGCCAGCACCTCTCATTCCCACCCGTTTCG<br>GAGGTCAAGGGGTCATCCAAATTCCTCAGCAAATGCAACAAG<br>(SEQ ID NO: 32) |
| protein phos-phatase 1 alpha at 96a | TATGTGTACGTGTGCCCGTTCGTGCTCCTCGCTCTTCTCGTCTAATTCTTG<br>TCGATTTTCGTTTGCAATTAAACACATAATTTATCACTCTTTGATGATAA<br>TGTTATATTTTTAGAGAAATTCGCGCAAGGGGGCGCATTTATTTTTGTAC<br>TTTTCGTTTTAGCGAATTCGTAGTAATTAATTAATTTTTAATGGGGAATT<br>ACGTGATATAAGGCTGAAAAGAAATATTTAATGTGTATAACCGATGAT<br>ACAAAACGGGAAGTATAATGTAGTTTAGCTAACGAAGAAAGTGGCTGA<br>TTATTTTTAGGTGATTCTTTGATTTTTATTCTTCTGGGCTAATTATAAATG<br>GGAAAATACTACTTGTTTCCATTGAACAAATCAGTAATCGTTAAATTATT<br>AAAATGTACTTATTTCTCTCTTTTATCTCTGTACTTACAAAAATCATGAC<br>TACTAAGTAAAAGTTTCATTCTCTCTGTTGTATAATATTTGCAATTAATT<br>ATGGTTACCAACGTTTCGCTTGCTCTTCATCAA (SEQ ID NO: 33) |
| regulatory particle non-atpase 7 | TTGAAGAGGGAGGTGATTGGGACAGAAGAAATCGTTTGAAAGTTTATC<br>AAGGCGTGTATAATATGGCTGTTAGGGATTTCAAAACTGCTGCAAACAT<br>GTTCTTGGACACAATAAGTACTTTCACGTCATATGAATTAATGGATTATA<br>AGTCATTTGTGCGTTACACAGTCTATGTTTCAATGATAAGTTTACCAAGA<br>TATGAACTACGAGACAAAGTGATAAAAGGCTCGGAGATACTGGAAGTT<br>TTGCATTCTGAACCCCAAGTAAAAGATTATTTGTTTTCTTTGTACAACTG<br>TCAGTATTCAGAATTTTTCATAAACTTAGCTGAAGTTGAGAGAAACTTTC<br>GCAAAGACTATTTGTTAAATCCACACTACCGTTATTATGTAAGAGAGAT<br>GAGAATATTGGCTTATTCACAGTTACTGGAATCTTATCGTTCTTTAACGT<br>TACAATATATGGCCGAGGCTTTTGGCGTTTCTACTGACTTCATTGATGAA<br>GAATTGTCTCAGTTTATAGCCACAGGAAGACTTCATGCAAGAATTGATA<br>GGGTAGGTGGCATTGTTGAGACAAATAGGCCGGATCA<br>(SEQ ID NO: 34) |
| regulatory particle triple-a atpase 3 | GCCAAAGCAGTAGCACATCATACTACTGCTGCTTTTATTCGAGTTGTTGG<br>GTCTGAATTTGTTCAAAAATATCTGGGTGAAGGACCTCGAATGGTGAGG<br>GATGTTTTCAGACTTGCTAAAGAGAATGCACCAGCTATCATTTTCATTGA<br>TGAAATTGATGCAATTGCCACAAAAAGATTTGATGCTCAAACTGGAGCT<br>GATAGAGAGGTCCAGAGAATCCTTTTGGAACTTCTCAATCAAATGGATG<br>GTTTTGATCAAACTACTAATGTTAAGGTTATTATGGCAACCAATAGGGC<br>AGACACTTTGGATCCTGCTTTACTTCGTCCTGGTCGTTTGGACAGGAAAA<br>TAGAATTTCCTCTGCCAGACCGTAGACAAAAACGTCTCATTTTCAGCAC<br>AATTACTTCAAAAATGAACCTTTCTGAAGAGGTTGATTTGGAAGATTAT<br>GTAGCAAGACCAGATCGTATTTCTGGGGCTGATATTAATGCCATTTGTC<br>AAGAAGCTGGAATGCATGCT (SEQ ID NO: 35) |
| Actin | GCTAACCGCGAGAAGATGACTCAAATCATGTTCGAAACCTTCAACACCC<br>CAGCCATGTACGTCGCTATTCAAGCTGTACTTTCTCTGTATGCCTCTGGT<br>CGTACCACCGGTATCGTCTTAGATTCTGGAGACGGTGTTTCTCACACTGT<br>ACCCATCTATGAAGGTTACGCTTTACCCCATGCCATCCTCCGTTTGGACT<br>TGGCCGGTCGTGACTTGACCGACTACCTCATGAAGATCTTGACCGAAAG<br>AGGCTACTCATTCACAACCACCGCTGAAAGAGAAATTGTTAGGGACATC<br>AAGGAAAAACTTTGCTATGTTGCTTTGGACTTCGAACAAGAAATGGCCA<br>CAGCCGCTGCCTCCACCTCTCTGGAGAAGAGCTACGAATTGCCTGATGG<br>ACAGGTCATCACTGTTGGAAACGAAAGGTTCC (SEQ ID NO: 36) |
| cactus | ATGTTGTGTTGGTGCGAAAAGTCGCGTTTTCAATGAAATTTTCTTATACC<br>GGTACCAAATGCCGCGCAGTGAACTGTTTATGATTAATATCCAACATCT<br>TACCAATGATTTTCCAAGAAAAACGGCGCCTGGAATGACCGAGGACGA<br>AAAGACTGACTGCGATTCGAGGACAGACAGCGGTTTTTTGTCGGGTGGA<br>AATTTGGCATTATCAGGTGAAATAATTTCGGAAGAGATCCCTCCAACTC<br>CGACCTCGGCAGATGACCATAAAAAACAGGCTCTCATCGACGATAACTT<br>GATGCGTTTAGATAGTGGTGTAGACCTTGGTTTGTCCGAAAGTTTTTCAA<br>GCCTGAGTTTGAAAAATTCGGGACTCAACGACCTTAGTTCGGGAA<br>(SEQ ID NO: 37) |
| alpha snap | GTAGTGCATTTTGCGAAGCAGGAAATTTACATTTGAAAACTGGCTCTCG<br>ACATGATGCCGCAACTAATTTTGTTGATGCTGCTAACTGTTATAAAAAG<br>TCTGATATTAATGAGGCAGTCAACTGTCTTGTAAGAGCAATAGAAATAT<br>ACACTGACATGGGGCGCTTTACTATGGCTGCAAAACATCACCAAAGCAT |

TABLE 4-continued

Sequences of dsRNA for EAB

| Gene target | dsRNA sequence (subsequence of mRNA target) |
|---|---|
| | TGCAGAGATGTATGAAACTGATGCAGCCGATCTCAAGAAAGCAGTTCA<br>ACATTATGAACAAGCTGCAGATTACTACAGGGGTGAAGAAAGCAATTC<br>ATCTGCCAACAAGTGTCTTTTAAAAGTTGCCCAATATGCAGCACAGCTA<br>GAAGATTATACAAAAGCTATTCAGATCTACGAGCAAGTAGCTTCATCTT<br>CATTAGAGAACTCTTTGCTGAAGTACAGTGCAAAGGAGTATTTGTTTCG<br>TGCTGCTCTTTGTCACCTGTGTGTAGATTTGCTGAATGCTCGTCA<br>(SEQ ID NO: 38) |
| inverse regulator a | ACCGGTGTTACCAAAGCAAGTACTGGTAAGATTGTTCCTGTTTCTGGTG<br>GTTCTTCGGTAGATCCAGAAACTCTAAGCATGCAACAGAAACTTATAAA<br>CAAACAGAAGGAGTTGCTGGAGCTGCAACAGCGCAAACTTGAGTTAGA<br>ACTTCTACAAACCCAAGTTAGACTGCAAGAACAACTAAAAGGAAAAAT<br>TGTATCTAGCTCTACGTCAGATACTAAAACTGTCACATCACAGAAAACC<br>ACTTCTGCTCATTCTCAGAATTTACTTTTAAAACCCGGGGTAACTAAAGA<br>ATTGTCTCCGACTATAAACGTGAAGCCCTCAACTGGCAGTAATTTAAGA<br>AGCAAATATTCACAGAGTTTGTCAGCTATGAAAAGTAAGTTACTGCAGC<br>AACAGCAAACCGCATCAGATCAGACTACAACACCACATGTAGCGCCTGT<br>TAATAGCGC (SEQ ID NO: 39) |
| heat shock 70-kDa protein cognate 3 | GTTACGAGCCAGGGTGAAAAGATCTTTGCCCCTGAAGAAATTTCTGCCA<br>TGGTCTTGGGCAAAATGAAAGAGACTGCTGAAGCTTACCTTGGTAAAAA<br>AGTTACCCATGCTGTTGTAACAGTACCAGCATATTTCAATGATGCTCAG<br>AGACAGGC CACCAAAGACGCCGGTGTTATTGCTGGACTTAATGTTATGA<br>GAATTATCAATGAACCTACAGCTGCTGCCATTGCATATGGTATGGATAA<br>GAAAGAAGGGGAAAAGAATGTGTTAGTCTTTGATTTGGGTGGTGGAAC<br>CTTTGATGTTTCCCTCCTTACCATTGATAATGGAGTCTTTGAGGTGGTGG<br>CTACAAATGGTGACACTCATTTGGGTGGCGAAGACTTCGATCAGCGTGT<br>TATGGACCACTTTATCAAGC TGTACAAAAAGAAGAAGGGC AAAGACAT<br>TCGCAAAGATAACCGTGCCGTTCAAAAG (SEQ ID NO: 40) |
| gawky | CAACATTGCGCCGACTACTACGAATAATAATGTTAACAATACGACTTCA<br>ACGAATACGACCAAGCAGCAATTAGAGCAGCTGAATAATATGCGAGAA<br>GCTATCTTTAGCCACGATGGATGGGGAGGCCATATTAATCAAGATACGA<br>CGTGGGAAATTCCGGGAAGTCCGGAGCCTCCCATAAAATTGGATGGTAC<br>GAACGCGCCTCCTTGGAAACCAACAGTCAACAATGGGACAGAATTATG<br>GGAAGCAAATTTGCGTAATGGTGGTCAACCACCTCCTCAACCCCAGCAA<br>AAAACGCCTTGGGGCCACACACCATTAACCAATATTGGCGGCACATGGG<br>GCGAAGATGATGATGTCGCGGATACCTCTAATGTGTGGACGGGTGTTCC<br>ATCAGGACAACAGCAATGGGGAAATACAGGAAACAGTGGAGGAGGAA<br>TGTGG (SEQ ID NO: 41) |

EAB dsRNA Effect on *Tribolium castaneum*.

To evaluate potential off-target effects of the EAB-specific dsRNA, both EAB.dsHSP and EAB.dsSHI or dsGFP as a control were injected into *T. castaneum* adults. For microinjections, 10-18 adults were anesthetized on ice and temporarily fixed on a glass slide using double-sided tape. 0.1 mL of 5 mg/mL dsRNA (0.5 mg/adult) was injected into the dorsal side of its first or second abdominal segment using Nanoject III Programmable Nanoliter Injector (Drummond Scientific Company, Broomall, Pa., USA). After dsRNA injections insects were place in 12-well plates with wheat flour and held in darkness at 26° C. and 36% humidity. Insect mortality was recorded 10 d post-dsRNA injection. Sun-Shepard's formula[30] was used to adjust for mortality of controls. Bioinformatic analyses were performed to compare the sequences of gene fragment used for dsRNA synthesis from EAB and *T. castaneum*. Sequences of hsp and shi gene regions used for dsRNA synthesis from EAB were aligned to *T. castaneum* genes using MUSCLE software Evaluation of EAB-Specific dsRNAs for Non-Target Effects on Model Insects: Colorado Potato Beetle.

Figure 8:
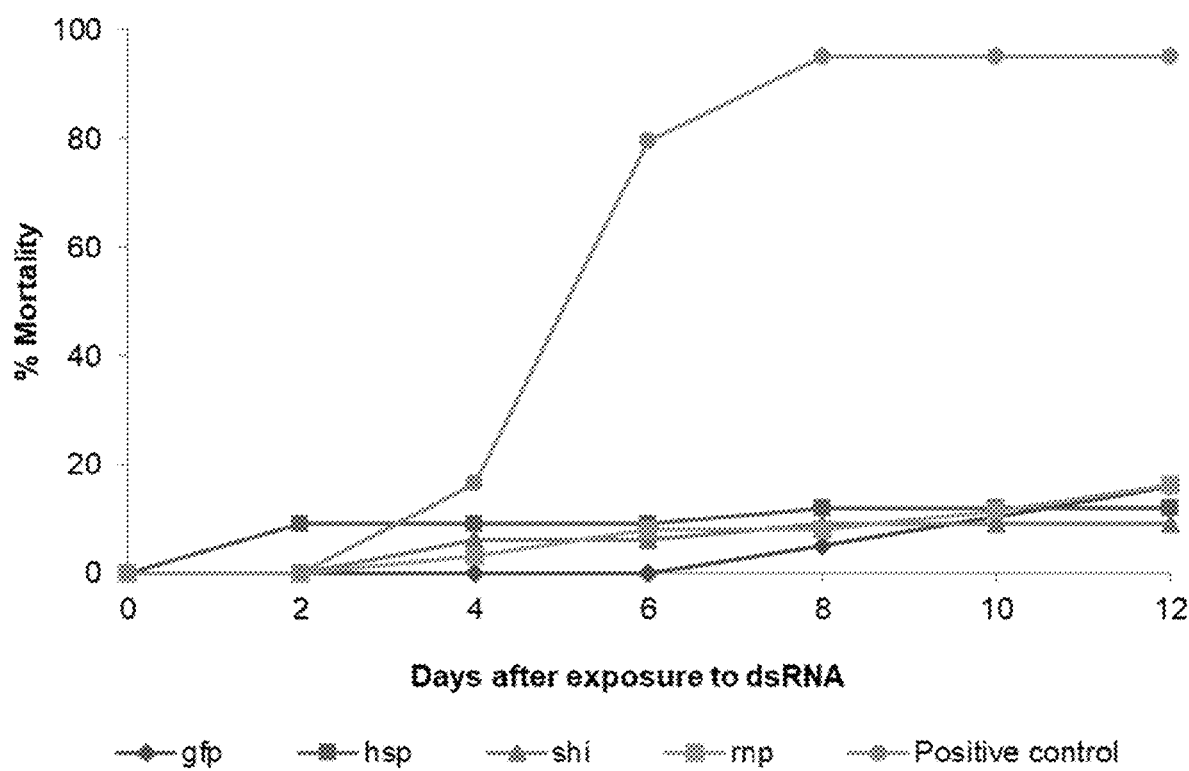
FIG. 8 shows Second instar CPB larval mortality after exposure to EAB dsRNAs (10 μg/μL) targeting the genes hsp, shi and rnp; 10 μg/μL of dsGFP was used as negative control and 10 μg/μL of dsACT was used as positive control.

No lethal effect on a model herbivore, the Colorado potato beetle, *Leptinotarsa decemlineata* (Coleoptera: Chrysomelidae) FIG. 8.

Evaluation of EAB-Specific dsRNAs for Non-Target Effects on Model Insects: The Spotted Lady Beetle.

Figure 9A:
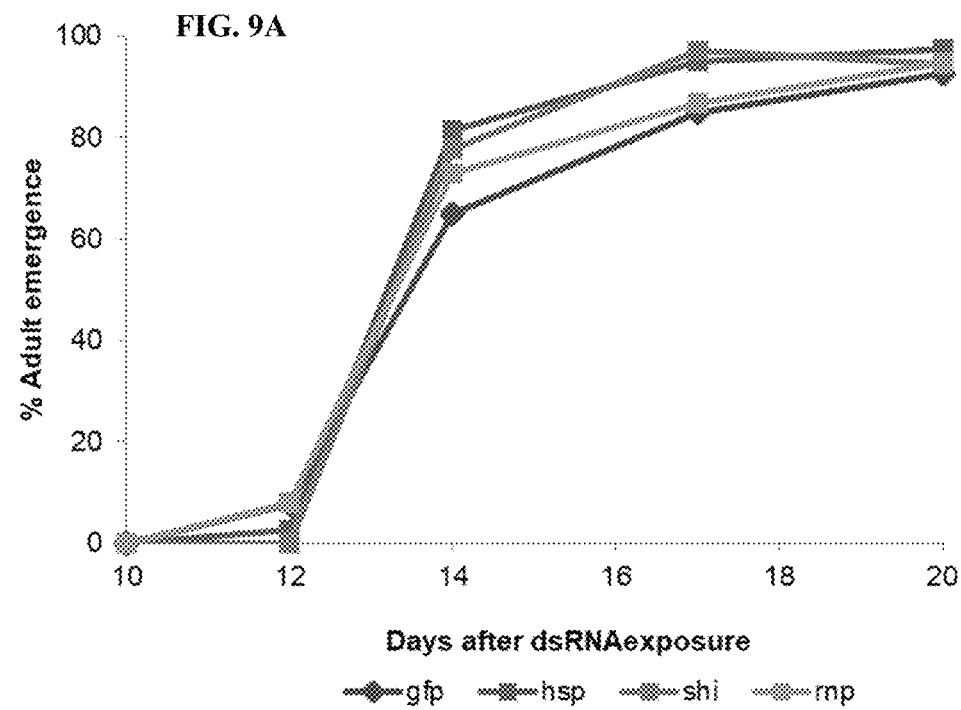
FIG. 9A shows Spotted lady beetle larval mortality after exposure to EAB dsRNAs (10 μg/μL) targeting the genes hsp, shi and rnp; 10 μg/μL of dsGFP was used as negative control and 10 μg/μL of dsvATPase was used as positive control.
Figure 9B:
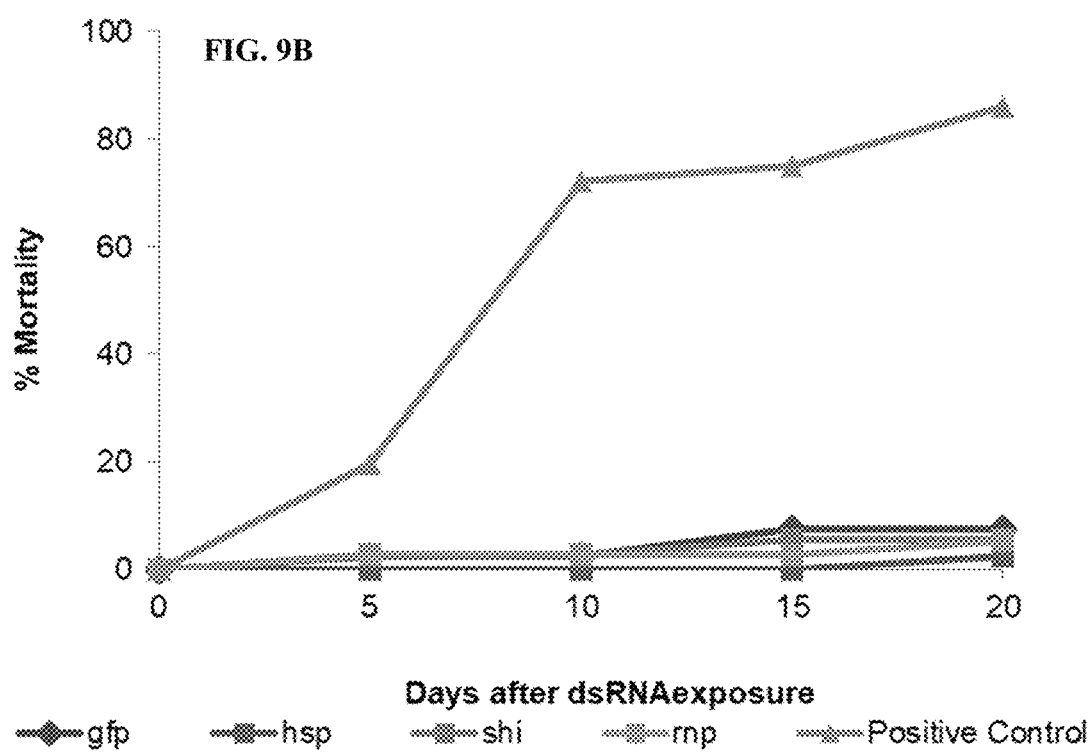
FIG. 9B shows Spotted lady beetle subsequent adult emergence from day 12 until day 20 after exposure to EAB dsRNAs (10 μg/μL) targeting the genes hsp, shi and rnp; 10 μg/μL of dsGFP was used as negative control and 10 μg/μL of dsvATPase was used as positive control.

No lethal or sublethal effects on a model predator, the spotted lady beetle, *Coleomegilla maculata* (Coleoptera: Coccinellidae) FIG. 9.

Evaluation of EAB-Specific dsRNAs for Nontarget Effects on Model Insects: The Honeybee.

Figure 10A:
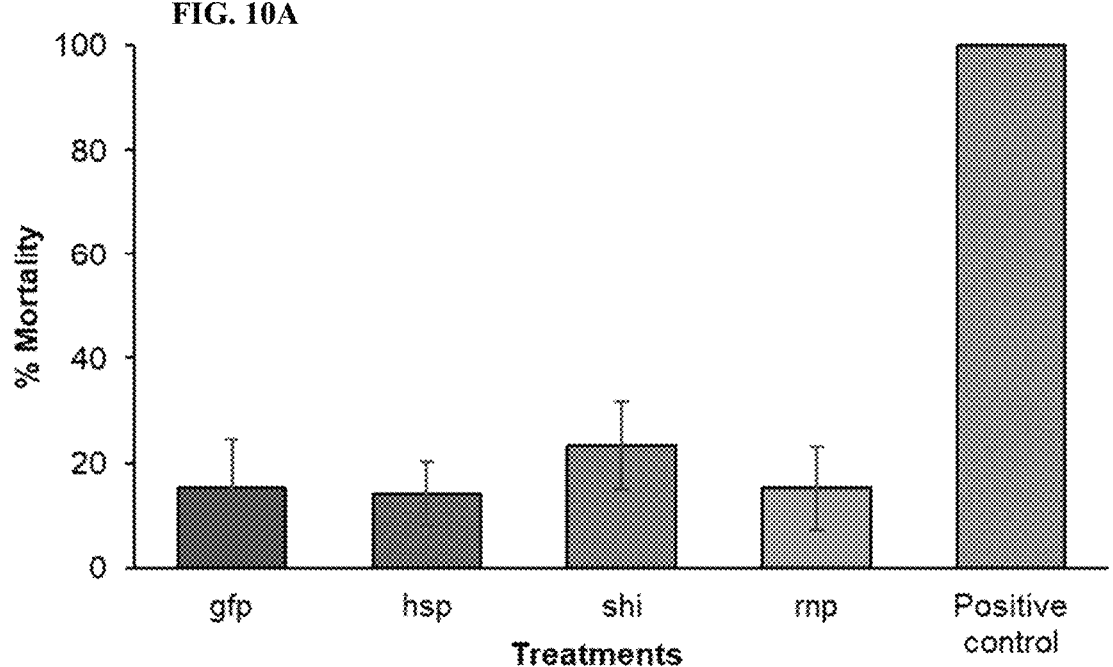
FIG. 10A shows Worker bees <24 hours after emergence were exposed to EAB-specific dsRNAs targeting the genes hsp, shi, and rnp at a concentration of 10 μg per individual; 10 μg per individual of dsGFP was used as negative control and 0.05 μg/μL of potassium arsenate was used as positive control. Adult mortality was evaluated daily for 30 days after ingestion of the dsRNAs. Mortality after 10 days.
Figure 10B:
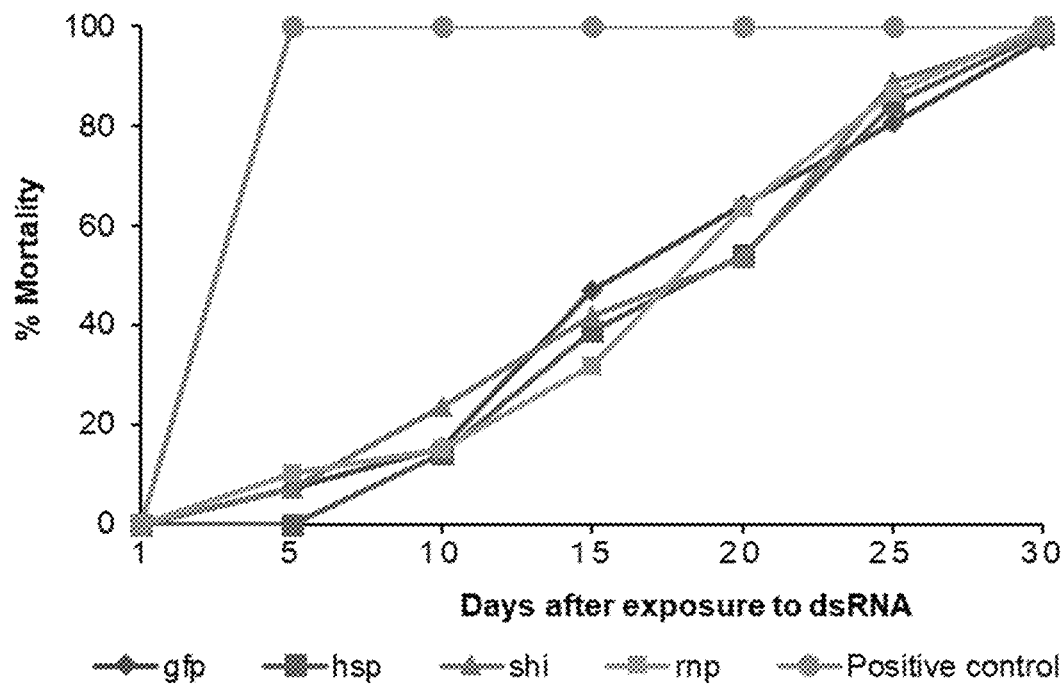
FIG. 10B shows Worker bees <24 hours after emergence were exposed to EAB-specific dsRNAs targeting the genes hsp, shi, and rnp at a concentration of 10 μg per individual; 10 μg per individual of dsGFP was used as negative control and 0.05 μg/μL of potassium arsenate was used as positive control. Adult mortality was evaluated daily for 30 days after ingestion of the dsRNAs. mortality over the 30 day assay.

No lethal effect on a model pollinator, the European honeybee, *Apis mellifera* (Hymenoptera: Apidae) FIG. 10.

Evaluation of EAB-Specific dsRNAs for Nontarget Effects on Classical Biological Control Agents.

Figure 11A:
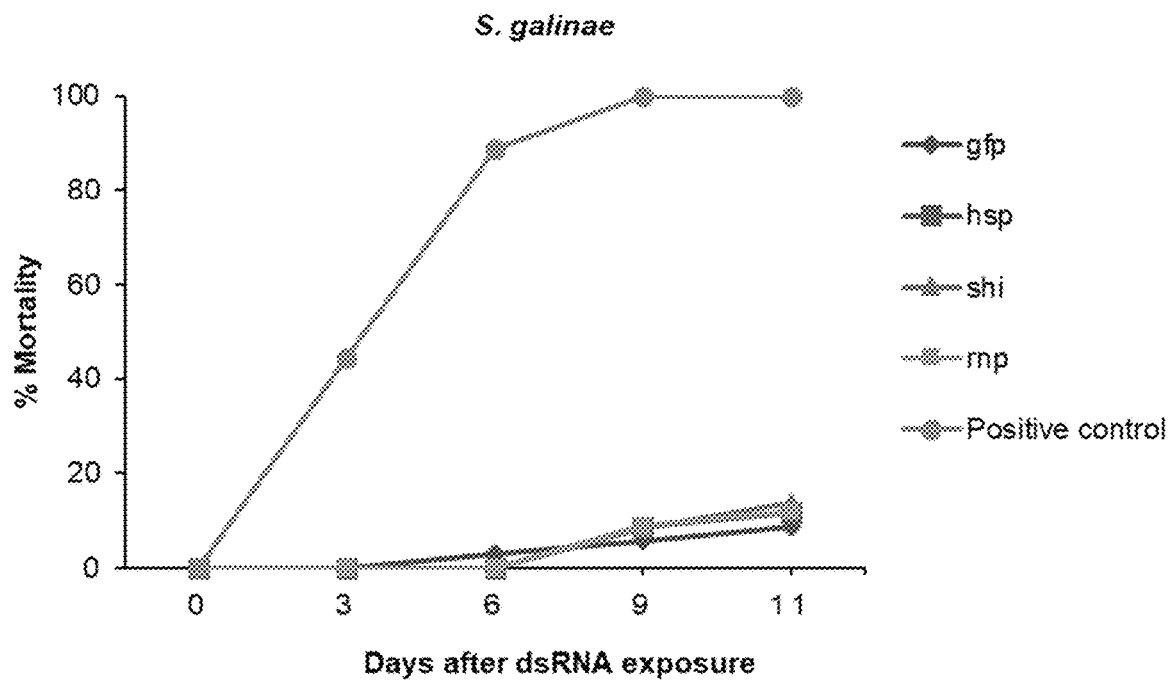
FIG. 11A. shows Mortality of the classical biological control agents, the parasitic (a) *Tetrastichus planipennis* exposed to dsRNAs at 10 μg/μL.
Figure 11B:
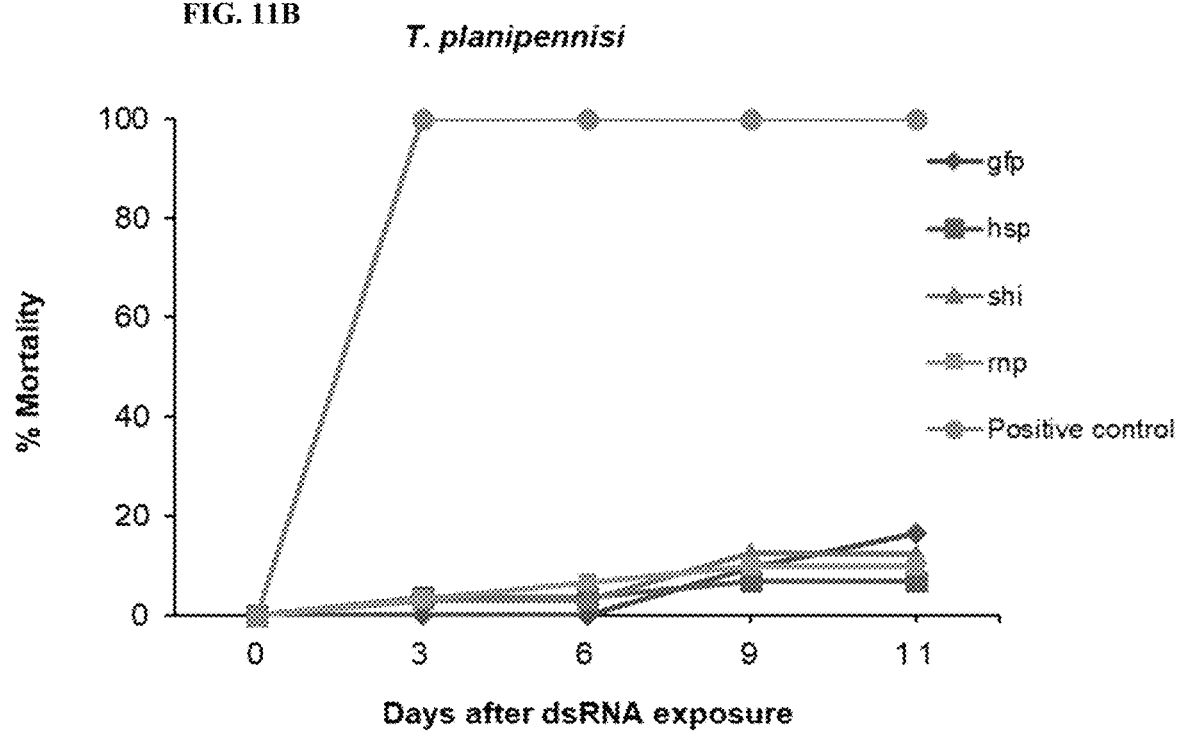
FIG. 11B shows Mortality of the classical biological control agents, the parasitic *Spathius galinae* exposed to dsRNAs at 10 μg/μL.

No lethal effect on the classical biological control agents deployed for EAB management, the parasitoids *Tetrastichus planipennisi* (Hymenoptera: Eulophidae) and *Spathius galinae* (Hymenoptera: Braconidae) FIG. 11.

All publications, patents, and patent applications mentioned in this specification are herein incorporated by reference to the same extent as if each individual publication, patent, or patent application was specifically and individually indicated to be incorporated by reference, including the references set forth in the following list:

REFERENCES

1. Bachman, P. M. et al. Ecological risk assessment for DvSnf7 RNA: A plant-incorporated protectant with targeted activity against western corn rootworm. Regul Toxicol Pharmacol 81, 77-88, https://doi.org/10.1016/j.yrtph.2016.08.001 (2016).

2. Joga, M. R., Zotti, M. J., Smagghe, G. & Christiaens, O. RNAi Efficiency, Systemic Properties, and Novel Delivery Methods for Pest Insect Control: What We Know So Far. Frontiers in Physiology 7, 553, https://doi.org/10.3389/fphys.2016.00553 (2016).
3. Burand, J. P. & Hunter, W. B. RNAi: Future in insect management. J Invertebr Pathol 112, S68-S74, https://doi.org/10.1016/j. jip.2012.07.012 (2013).
4. Palli, S. R. RNAi methods for management of insects and their pathogens. DNA 5, 3 (2012).
5. Gamborg, C. & Sandøe, P. Ethical considerations regarding genetically modified trees. IUFRO Forests and Genetically Modified Trees. Food and Agriculture Organization of the United Nations, Rome, 163-176 (2010).
6. Fladung, M., Pasonen, H. & Walter, C. Genetically modified trees and associated environmental concerns. IUFRO forests and genetically modified trees. Food and Agriculture Organization of the United Nations, Rome, 177-202 (2010).
7. Hong, S. W., Jiang, Y., Kim, S., Li, C. J. & Lee, D.-K. Target Gene Abundance Contributes to the Efficiency of siRNA-Mediated Gene Silencing. Nucleic Acid Therapeutics 24, 192-198, https://doi.org/10.1089/nat.2013.0466 (2014).
8. Baum, J. A. et al. Control of coleopteran insect pests through RNA interference. Nat Biotechnol 25, 1322-1326, https://doi. org/10.1038/nbt1359 (2007).
9. Ulrich, J. et al. Large scale RNAi screen in *Tribolium* reveals novel target genes for pest control and the proteasome as prime target. BMC Genomics 16, https://doi.org/10.1186/s12864-015-1880-y (2015).
10. Whyard, S., Singh, A. D. & Wong, S. Ingested double-stranded RNAs can act as species-specific insecticides. Insect Biochem Mol Biol 39, 824-832, https://doi.org/10.1016/j.ibmb.2009.09.007 (2009).
11. Rodrigues, T. B. et al. S. R. Development of RNAi method for screening candidate genes to control emerald ash borer, *Agrilus planipennis*. Scientific Reports 7,7379, https://doi.org/10.1038/s41598-017-07605-x (2017).
12. Scott, J. G. et al. Towards the elements of successful insect RNAi. J Insect Physiol 59, 1212-1221, https://doi.org/10.1016/j.jinsphys.2013.08.014 (2013).
13. Häggman, H. et al. Genetically engineered trees for plantation forests: key considerations for environmental risk assessment. Plant Biotechnol J 11, 785-798, https://doi.org/10.1111/pbi.12100 (2013).
14. Zhu, F., Xu, J. J., Palli, R., Ferguson, J. & Palli, S. R. Ingested RNA interference for managing the populations of the Colorado potato beetle. *Leptinotarsa decemlineata*. Pest Manage Sci 67, 175-182, https://doi.org/10.1002/ps.2048 (2011).
15. Palli, S. R. RNA interference in colorado potato beetle: steps toward development of dsRNA as a commercial insecticide. Current Opinion in Insect Science 6, 1-8, https://doi.org/10.1016/j.cois.2014.09.011 (2014).
16. Hu, J., Angeli, S., Schuetz, S., Luo, Y. & Hajek, A. E. Ecology and management of exotic and endemic Asian longhorned beetle *Anoplophora glabripennis*. Agricultural and Forest Entomology 11, 359-375 (2009).
17. Herms, D. A. & McCullough, D. G. Emerald ash borer invasion of North America: history, biology, ecology, impacts, and management. Annu Rev Entomol 59, 13-30, https://doi.org/10.1146/annurev-ento-011613-162051 (2014).
18. Rodrigues, T. B., Dhandapani, R. K., Duan, J. J. & Palli, S. R. RNA interference in the Asian Longhorned Beetle: Identification of Key RNAi Genes and Reference Genes for RT-qPCR. Scientific Reports 7, 8913, https://doi.org/10.1038/s41598-017-08813-1 (2017).
19. Wang, K. et al. Variation in RNAi efficacy among insect species is attributable to dsRNA degradation in vivo. Insect Biochem Mol Biol 77, 1-9, https://doi.org/10.1016/j.ibmb.2016.07.007 (2016).
20. Herms, D. A. et al. Insecticide options for protecting ash trees from emerald ash borer. North central IPM center bulletin 12 (2009).
21. Duan, J. J., Abell, K. J., Bauer, L. S., Gould, J. & Van Driesche, R. Natural enemies implicated in the regulation of an invasive pest: a life table analysis of the population dynamics of the emerald ash borer. Agricultural and Forest Entomology 16, 406-416 (2014).
22. Davidson, W. & Rieske, L. K. Establishment of classical biological control targeting emerald ash borer is facilitated by use of insecticides, with little effect on native arthropod communities. Biological Control 101, 78-86 (2016).
23. Li, X. X., Dong, X. L., Zou, C. & Zhang, H. Y. Endocytic pathway mediates refractoriness of insect *Bactrocera dorsalis* to RNA interference. Scientific Reports 5, https://doi.org/10.1038/srep08700 (2015).
24. Galdeano, D. M., Breton, M. C., Lopes, J. R. S., Falk, B. W. & Machado, M. A. Oral delivery of double-stranded RNAs induces mortality in nymphs and adults of the Asian citrus psyllid, *Diaphorina citri*. Plos One 12, e0171847, https://doi.org/10.1371/journal.pone.0171847 (2017).
25. Miller, S. C., Miyata, K., Brown, S. J. & Tomoyasu, Y. Dissecting Systemic RNA Interference in the Red Flour Beetle *Tribolium castaneum*: Parameters Affecting the Efficiency of RNAi. Plos One 7, e47431, https://doi.org/10.1371/journal.pone.0047431 (2012).
26. Taning, C. N. T., Andrade, E. C., Hunter, W. B., Christiaens, O. & Smagghe, G. Asian Citrus Psyllid RNAi Pathway—RNAi evidence. Scientific Reports 6, https://doi.org/10.1038/srep38082 (2016).
27. Andrade, E. C. & Hunter, W. B. RNAi feeding bioassay: development of a non-transgenic approach to control Asian citrus psyllid and other hemipterans. Entomol Exp Appl 162, 389-396, https://doi.org/10.1111/eea.12544 (2017).
28. Rajarapu, S. P., Mamidala, P. & Mittapalli, O. Validation of reference genes for gene expression studies in the emerald ash borer (*Agrilus planipennis*). Insect Sci 19, 41-46, https://doi.org/10.1111/j.1744-7917.2011.01447.x (2012).
29. Livak, K. J. & Schmittgen, T. D. Analysis of Relative Gene Expression Data Using RealTime Quantitative PCR and the 2-$\Delta\Delta$Ct Method. Methods 25, 402-408, https://doi.org/10.1006/meth.2001.1262 (2001).
30. Puntener, W. Manual for field trials in plant protection. Second Edition edn (Ciba-Geigy Limited, 1981).

It will be understood that various details of the presently disclosed subject matter can be changed without departing from the scope of the subject matter disclosed herein. Furthermore, the foregoing description is for the purpose of illustration only, and not for the purpose of limitation.

The invention claimed is:

1. A method of inducing RNAi in an insect of the Coleoptera order, comprising:
administering dsRNA to the insect, wherein a total dsRNA includes a combination of dsRNAs targeting the genes inhibitor of apoptosis (IAP), shibire (SHI), heat shock 70-kDa protein cognate 3 (HSP), and U1 small nuclear ribonucleoprotein (RNP).

2. The method of claim 1, wherein the total dsRNA is administered once daily for 1, 2, 3, 4, 5, 6, 7, or 8 days.

3. The method of claim 1, wherein the total dsRNA is administered once daily in an amount of about 1 μg/μL to about 20 μg/μL.

4. The method of claim 1, wherein the insect is *Agrilus planipennis*.

5. The method of claim 1, wherein the administration of the total dsRNA does not cause mortality in *Tribolium castaneum, Leptinotarsa decemlineata, Coleomegilla maculate, Apis mellifera, Tetrastichus planipennisi*, or *Spathius galinae*.

6. The method of claim 1, wherein administering dsRNA to the insect includes administering the total dsRNA in a composition that includes a sucrose solution.

7. A method of inducing RNAi in an insect of the Coleoptera order, comprising: administering dsRNA to the insect, wherein a total dsRNA includes a dsRNA targeting U1 small nuclear ribonucleoprotein (RNP).

* * * * *

SEQUENCE LISTING

<160> NUMBER OF SEQ ID NOS: 41

<210> SEQ ID NO 1
<211> LENGTH: 40
<212> TYPE: DNA
<213> ORGANISM: Artificial Sequence
<220> FEATURE:
<223> OTHER INFORMATION: EAB srp Forward Primer

<400> SEQUENCE: 1
taatacgact cactataggg ggctgtagca aatgcagtga           40

<210> SEQ ID NO 2
<211> LENGTH: 40
<212> TYPE: DNA
<213> ORGANISM: Artificial Sequence
<220> FEATURE:
<223> OTHER INFORMATION: EAB srp Reverse Primer

<400> SEQUENCE: 2
taatacgact cactataggg acgcgccata gactcttgtt           40

<210> SEQ ID NO 3
<211> LENGTH: 40
<212> TYPE: DNA
<213> ORGANISM: Artificial Sequence
<220> FEATURE:
<223> OTHER INFORMATION: EAB rop FORWARD PRIMER

<400> SEQUENCE: 3
taatacgact cactataggg gccgacacct ttcagtgttt           40

<210> SEQ ID NO 4
<211> LENGTH: 40
<212> TYPE: DNA
<213> ORGANISM: Artificial Sequence
<220> FEATURE:
<223> OTHER INFORMATION: EAB rop REVERSE PRIMER

<400> SEQUENCE: 4
taatacgact cactataggg gcttggaatc ggtgaacttt           40

<210> SEQ ID NO 5
<211> LENGTH: 40
<212> TYPE: DNA
<213> ORGANISM: Artificial Sequence
<220> FEATURE:
<223> OTHER INFORMATION: EAB shi FORWARD PRIMER

<400> SEQUENCE: 5
taatacgact cactataggg tggcacattt gtatgccagt           40

<210> SEQ ID NO 6
<211> LENGTH: 40
<212> TYPE: DNA
<213> ORGANISM: Artificial Sequence
<220> FEATURE:
<223> OTHER INFORMATION: EAB shi REVERSE PRIMER

<400> SEQUENCE: 6
taatacgact cactataggg cttgttgcat ttgctgagga           40

<210> SEQ ID NO 7
<211> LENGTH: 40
<212> TYPE: DNA
<213> ORGANISM: Artificial Sequence

```
<220> FEATURE:
<223> OTHER INFORMATION: EAB pp1a FORWARD PRIMER

<400> SEQUENCE: 7
taatacgact cactataggg tatgtgtacg tgtgcccgtt                    40

<210> SEQ ID NO 8
<211> LENGTH: 40
<212> TYPE: DNA
<213> ORGANISM: Artificial Sequence
<220> FEATURE:
<223> OTHER INFORMATION: EAB pp1a REVERSE PRIMER

<400> SEQUENCE: 8
taatacgact cactataggg ttgatgaaga gcaagcgaaa                    40

<210> SEQ ID NO 9
<211> LENGTH: 40
<212> TYPE: DNA
<213> ORGANISM: Artificial Sequence
<220> FEATURE:
<223> OTHER INFORMATION: EAB rpn7 FORWARD PRIMER

<400> SEQUENCE: 9
taatacgact cactataggg ttgaagaggg aggtgattgg                    40

<210> SEQ ID NO 10
<211> LENGTH: 40
<212> TYPE: DNA
<213> ORGANISM: Artificial Sequence
<220> FEATURE:
<223> OTHER INFORMATION: EAB rpn7 REVERSE PRIMER

<400> SEQUENCE: 10
taatacgact cactataggg tgatccggcc tatttgtctc                    40

<210> SEQ ID NO 11
<211> LENGTH: 40
<212> TYPE: DNA
<213> ORGANISM: Artificial Sequence
<220> FEATURE:
<223> OTHER INFORMATION: EAB rpt3 FORWARD PRIMER

<400> SEQUENCE: 11
taatacgact cactataggg gccaaagcag tagcacatca                    40

<210> SEQ ID NO 12
<211> LENGTH: 40
<212> TYPE: DNA
<213> ORGANISM: Artificial Sequence
<220> FEATURE:
<223> OTHER INFORMATION: EAB rpt3 REVERSE PRIMER

<400> SEQUENCE: 12
taatacgact cactataggg agcatgcatt ccagcttctt                    40

<210> SEQ ID NO 13
<211> LENGTH: 40
<212> TYPE: DNA
<213> ORGANISM: Artificial Sequence
<220> FEATURE:
<223> OTHER INFORMATION: EAB act1 FORWARD PRIMER

<400> SEQUENCE: 13
taatacgact cactataggg gctaaccgcg agaagatgac                    40
```

<210> SEQ ID NO 14
<211> LENGTH: 40
<212> TYPE: DNA
<213> ORGANISM: Artificial Sequence
<220> FEATURE:
<223> OTHER INFORMATION: EAB act1 REVERSE PRIMER

<400> SEQUENCE: 14
taatacgact cactataggg ggaacctttc gtttccaaca                    40

<210> SEQ ID NO 15
<211> LENGTH: 40
<212> TYPE: DNA
<213> ORGANISM: Artificial Sequence
<220> FEATURE:
<223> OTHER INFORMATION: EAB cact FORWARD PRIMER

<400> SEQUENCE: 15
taatacgact cactataggg atgttgtgtt ggtgcgaaaa                    40

<210> SEQ ID NO 16
<211> LENGTH: 40
<212> TYPE: DNA
<213> ORGANISM: Artificial Sequence
<220> FEATURE:
<223> OTHER INFORMATION: EAB cact REVERSE PRIMER

<400> SEQUENCE: 16
taatacgact cactataggg ttcccgaact aaggtcgttg                    40

<210> SEQ ID NO 17
<211> LENGTH: 40
<212> TYPE: DNA
<213> ORGANISM: Artificial Sequence
<220> FEATURE:
<223> OTHER INFORMATION: - EAB asnap FORWARD PRIMER

<400> SEQUENCE: 17
taatacgact cactataggg gtagtgcatt ttgcgaagca                    40

<210> SEQ ID NO 18
<211> LENGTH: 40
<212> TYPE: DNA
<213> ORGANISM: Artificial Sequence
<220> FEATURE:
<223> OTHER INFORMATION: EAB asnap REVERSE PRIMER

<400> SEQUENCE: 18
taatacgact cactataggg tgacgagcat tcagcaaatc                    40

<210> SEQ ID NO 19
<211> LENGTH: 40
<212> TYPE: DNA
<213> ORGANISM: Artificial Sequence
<220> FEATURE:
<223> OTHER INFORMATION: EAB inra FORWARD PRIMER

<400> SEQUENCE: 19
taatacgact cactataggg accggtgtta ccaaagcaag                    40

<210> SEQ ID NO 20
<211> LENGTH: 40
<212> TYPE: DNA
<213> ORGANISM: Artificial Sequence
<220> FEATURE:
<223> OTHER INFORMATION: EAB inra REVERSE PRIMER -continued

```
<400> SEQUENCE: 20
taatacgact cactataggg gcgctattaa caggcgctac                               40

<210> SEQ ID NO 21
<211> LENGTH: 40
<212> TYPE: DNA
<213> ORGANISM: Artificial Sequence
<220> FEATURE:
<223> OTHER INFORMATION: EAB hsc70-3 FORWARD PRIMER

<400> SEQUENCE: 21
taatacgact cactataggg gttacgagcc agggtgaaaa                               40

<210> SEQ ID NO 22
<211> LENGTH: 40
<212> TYPE: DNA
<213> ORGANISM: Artificial Sequence
<220> FEATURE:
<223> OTHER INFORMATION: EAB hsc70-3 REVERSE PRIMER

<400> SEQUENCE: 22
taatacgact cactataggg cttttgaacg gcacggttat                               40

<210> SEQ ID NO 23
<211> LENGTH: 40
<212> TYPE: DNA
<213> ORGANISM: Artificial Sequence
<220> FEATURE:
<223> OTHER INFORMATION: EAB gw FORWARD PRIMER

<400> SEQUENCE: 23
taatacgact cactataggg caacattgcg ccgactacta                               40

<210> SEQ ID NO 24
<211> LENGTH: 40
<212> TYPE: DNA
<213> ORGANISM: Artificial Sequence
<220> FEATURE:
<223> OTHER INFORMATION: EAB gw REVERSE PRIMER

<400> SEQUENCE: 24
taatacgact cactataggg ccacattcct cctccactgt                               40

<210> SEQ ID NO 25
<211> LENGTH: 20
<212> TYPE: DNA
<213> ORGANISM: Artificial Sequence
<220> FEATURE:
<223> OTHER INFORMATION: T7 POLYMERASE PROMOTER SEQUENCE

<400> SEQUENCE: 25
taatacgact cactataggg                                                    20

<210> SEQ ID NO 26
<211> LENGTH: 20
<212> TYPE: DNA
<213> ORGANISM: Artificial Sequence
<220> FEATURE:
<223> OTHER INFORMATION: EAB shi FORWARD PRIMER

<400> SEQUENCE: 26
gggatctgcc caaattaaca                                                    20

<210> SEQ ID NO 27
```

```
<211> LENGTH: 20
<212> TYPE: DNA
<213> ORGANISM: Artificial Sequence
<220> FEATURE:
<223> OTHER INFORMATION: EAB shi REVERSE PRIMER

<400> SEQUENCE: 27
cccgtctgag ttctttctcg                                              20

<210> SEQ ID NO 28
<211> LENGTH: 20
<212> TYPE: DNA
<213> ORGANISM: Artificial Sequence
<220> FEATURE:
<223> OTHER INFORMATION: EAB hsp70-3 FORWARD PRIMER

<400> SEQUENCE: 28
gacaaaggaa cgggaaacaa                                              20

<210> SEQ ID NO 29
<211> LENGTH: 20
<212> TYPE: DNA
<213> ORGANISM: Artificial Sequence
<220> FEATURE:
<223> OTHER INFORMATION: EAB hsp70-3 REVERSE PRIMER

<400> SEQUENCE: 29
tctcggcatc ccttatcatc                                              20

<210> SEQ ID NO 30
<211> LENGTH: 496
<212> TYPE: DNA
<213> ORGANISM: Artificial Sequence
<220> FEATURE:
<223> OTHER INFORMATION: srp54k dsRNA

<400> SEQUENCE: 30
ggctgtagca aatgcagtga aacctgataa tattattttt gttatggatg ctacaattgg    60
acaggcttgt gaagctcagg caaaagcatt taaagaaaag gttgatgtag ctccgtgat   120 tataacgaaa ttagatggcc acgctaaagg tggaggagcc ctaagtgcgg ttgcagcgac   180
gcaaagtcct ataatttta ttggtactgg agagcacata gatgacttag aaccatttaa    240
aacaaaacca tttattagca aattacttgg aatgggagat attgaagggt tgatagacaa   300
agtcaatgaa ttaaaattag aggacaatga agaacttta gaaagatca aacatggaca     360 gtttacgcta agggacatgt atgaacagtt ccaaaatatc atgaaaatgg gtccttttc    420 acaaataatg gggatgatac ccggttttag tcaaagtttt atgtcaaaag gtagtgaaca   480
agagtctatg gcgcgt                                                  496

<210> SEQ ID NO 31
<211> LENGTH: 493
<212> TYPE: DNA
<213> ORGANISM: Artificial Sequence
<220> FEATURE:
<223> OTHER INFORMATION: ras opposite dsRNA

<400> SEQUENCE: 31
gccgacacct ttcagtgttt ttatgatcct tcattttctg ctgcaagaac tgccaatatg    60
gagcgtatgg ccgaacagat tgcaaccctc tgtgctactc tcggggaata cccttcagtg   120
cgctatagag cggattggga caaaaatgta gaattagcac agttaatcca acaaaaacta   180
gacgcttata agcggatga accgacaatg ggtgaaggac cggaaaaagc tcgttcacaa    240
```

-continued

```
ctcttaattt tggacagagg gttcgattgt gtatcgcctc tcttacatga attaacattc      300
caggcaatgg cttacgattt attaccaatc gaaaacgacg tatatcgcta tgaagctacg      360
gcgggatcgg ctgaaaagaa ggaagttttg cttgacgaaa cgacgaattt gtgggtagaa      420
ttgcgtcatc agcacatcgc cgtcgtttct caaagtgtta ccaaaaattt gaaaagttc       480 accgattcca agc                                                         493
```

<210> SEQ ID NO 32
<211> LENGTH: 483
<212> TYPE: DNA
<213> ORGANISM: Artificial Sequence
<220> FEATURE:
<223> OTHER INFORMATION: shilbire dsRNA

<400> SEQUENCE: 32

```
tggcacattt gtatgccagt ggtgatcagc aacaaatgat ggaagaatca cctgaggaag      60
ccttgaagcg tgaagaaatg ttgcgaatgt accacgcatg taaagaagct ttaagaataa      120
taggagatgt ttcaatggct acagtatcca caccggtacc tccccccgta aagaatgact      180
ggctggcaag cggcttggat aatgcacgat tatcaccacc tagtccgggc gggagtaaac      240
gacaggctcc gttaatgagt caagttggtt catcgggatc gttaggttct tccggcaacg      300
tcagggctcc accgttgcct ccagcttcag gaagaccggc tcctgcgata cctaatcgac      360
ctggtggagg aatgcctccc atgccacctg gcagacctca aggacaacct ctgccagcac      420
ctctcattcc caccgtttc ggaggtcaag gggtcatcca aattcctcag caaatgcaac      480
aag                                                                   483
```

<210> SEQ ID NO 33
<211> LENGTH: 532
<212> TYPE: DNA
<213> ORGANISM: Artificial Sequence
<220> FEATURE:
<223> OTHER INFORMATION: Protein phosphatase 1 alpha dsRNA

<400> SEQUENCE: 33

```
tatgtgtacg tgtgcccgtt cgtgctcctc gctcttctcg tctaattctt gtcgattttc      60
gtttgcaatt aaacacataa tttatcactc tttgatgata atgttatatt tttagagaaa      120
ttcgcgcaag ggggcgcatt tattttttgta cttttcgttt tagcgaattc gtagtaatta     180
attaattttt aatggggaat tacgtgatat aaggctgaaa agaaatatt taatgtgtat       240 aaccgatgat acaaaacggg aagtataatg tagtttagct aacgaagaaa gtggctgatt      300
atttttaggt gattctttga ttttattct tctgggctaa ttataaatgg aaaatactα       360 cttgtttcca ttgaacaaat cagtaatcgt taaattatta aaatgtactt atttctctct      420
tttatctctg tacttacaaa aatcatgact actaagtaaa agtttcattc tctctgttgt      480
ataatatttg caattaatta tggttaccaa cgtttcgctt gctcttcatc aa              532
```

<210> SEQ ID NO 34
<211> LENGTH: 580
<212> TYPE: DNA
<213> ORGANISM: Artificial Sequence
<220> FEATURE:
<223> OTHER INFORMATION: regulatory particle non-atpase 7 dsRNA

<400> SEQUENCE: 34

```
ttgaagaggg aggtgattgg gacagaagaa atcgtttgaa agtttatcaa ggcgtgtata      60
```

```
atatggctgt tagggatttc aaaactgctg caaacatgtt cttggacaca ataagtactt      120
tcacgtcata tgaattaatg gattataagt catttgtgcg ttacacagtc tatgtttcaa      180
tgataagttt accaagatat gaactacgag acaaagtgat aaaaggctcg agatactgg       240 aagttttgca ttctgaaccc caagtaaaag attatttgtt ttctttgtac aactgtcagt      300
attcagaatt tttcataaac ttagctgaag ttgagagaaa ctttcgcaaa gactatttgt      360
taaatccaca ctaccgttat tatgtaagag agatgagaat attggcttat tcacagttac      420
tggaatctta tcgttcttta acgttacaat atatggccga ggcttttggc gtttctactg      480
acttcattga tgaagaattg tctcagttta tagccacagg aagacttcat gcaagaattg      540
atagggtagg tggcattgtt gagacaaata ggccggatca                            580
```

```
<210> SEQ ID NO 35
<211> LENGTH: 513
<212> TYPE: DNA
<213> ORGANISM: Artificial Sequence
<220> FEATURE:
<223> OTHER INFORMATION: regulatory particle triple-a atpase 3 dsRNA

<400> SEQUENCE: 35
gccaaagcag tagcacatca tactactgct gcttttattc gagttgttgg gtctgaattt       60
gttcaaaaat atctgggtga aggacctcga atggtgaggg atgttttcag acttgctaaa      120
gagaatgcac cagctatcat tttcattgat gaaattgatg caattgccac aaaaagattt      180
gatgctcaaa ctggagctga tagagaggtc cagagaatcc ttttggaact tctcaatcaa      240
atggatggtt ttgatcaaac tactaatgtt aaggttatta tggcaaccaa tagggcagac      300
actttggatc ctgctttact tcgtcctggt cgtttggaca ggaaaatagc atttcctctg      360
ccagaccgta gacaaaaacg tctcattttc agcacaatta cttcaaaaat gaacctttct      420
gaagaggttg atttggaaga ttatgtagca agaccagatc gtatttctgg ggctgatatt      480
aatgccattt gtcaagaagc tggaatgcat gct                                   513
```

```
<210> SEQ ID NO 36
<211> LENGTH: 427
<212> TYPE: DNA
<213> ORGANISM: Artificial Sequence
<220> FEATURE:
<223> OTHER INFORMATION: Actin dsRNA

<400> SEQUENCE: 36
gctaaccgcg agaagatgac tcaaatcatg ttcgaaacct tcaacacccc agccatgtac       60
gtcgctattc aagctgtact ttctctgtat gcctctggtc gtaccaccgg tatcgtctta      120
gattctggag acggtgtttc tcacactgta cccatctatg aaggttacgc tttacccccat     180 gccatcctcc gtttggactt ggccggtcgt gacttgaccg actacctcat gaagatcttg      240
accgaaagag gctactcatt cacaaccacc gctgaaagag aaattgttag ggacatcaag      300
gaaaaacttt gctatgttgc tttggacttc gaacaagaaa tggccacagc cgctgcctcc      360
acctctctgg agaagagcta cgaattgcct gatggacagg tcatcactgt tggaaacgaa      420
aggttcc                                                                427
```

```
<210> SEQ ID NO 37
<211> LENGTH: 389
<212> TYPE: DNA
<213> ORGANISM: Artificial Sequence
<220> FEATURE:
<223> OTHER INFORMATION: Cactus dsRNA
```

<400> SEQUENCE: 37

```
atgttgtgtt ggtgcgaaaa gtcgcgtttt caatgaaatt ttcttatacc ggtaccaaat      60
gccgcgcagt gaactgttta tgattaatat ccaacatctt accaatgatt ttccaagaaa     120
aacggcgcct ggaatgaccg aggacgaaaa gactgactgc gattcgagga cagacagcgg     180
ttttttgtcg ggtggaaatt tggcattatc aggtgaaata atttcggaag agatccctcc     240
aactccgacc tcggcagatg accataaaaa acaggctctc atcgacgata acttgatgcg     300
tttagatagt ggtgtagacc ttggtttgtc cgaaagtttt tcaagcctga gtttgaaaaa     360
ttcgggactc aacgacctta gttcgggaa                                        389
```

<210> SEQ ID NO 38
<211> LENGTH: 484
<212> TYPE: DNA
<213> ORGANISM: Artificial Sequence
<220> FEATURE:
<223> OTHER INFORMATION: alpha snap dsRNA

<400> SEQUENCE: 38

```
gtagtgcatt ttgcgaagca ggaaatttac atttgaaaac tggctctcga catgatgccg      60
caactaattt tgttgatgct gctaactgtt ataaaaagtc tgatattaat gaggcagtca     120
actgtcttgt aagagcaata gaaatataca ctgacatggg gcgctttact atggctgcaa     180
aacatcacca aagcattgca gagatgtatg aaactgatgc agccgatctc aagaaagcag     240
ttcaacatta tgaacaagct gcagattact acaggggtga agaaagcaat tcatctgcca     300
acaagtgtct tttaaaagtt gcccaatatg cagcacagct agaagattat acaaaagcta     360
ttcagatcta cgagcaagta gcttcatctt cattagagaa ctctttgctg aagtacagtg     420
caaaggagta tttgtttcgt gctgctcttt gtcacctgtg tgtagatttg ctgaatgctc     480
gtca                                                                  484
```

<210> SEQ ID NO 39
<211> LENGTH: 449
<212> TYPE: DNA
<213> ORGANISM: Artificial Sequence
<220> FEATURE:
<223> OTHER INFORMATION: inverse regulator a dsRNA

<400> SEQUENCE: 39

```
accggtgtta ccaaagcaag tactggtaag attgttcctg tttctggtgg ttcttcggta      60
gatccagaaa ctctaagcat gcaacagaaa cttataaaca aacagaagga gttgctggag     120
ctgcaacagc gcaaacttga gttagaactt ctacaaaccc aagttagact gcaagaacaa     180
ctaaaaggaa aaattgtatc tagctctacg tcagatacta aaactgtcac atcacagaaa     240
accacttctg ctcattctca gaatttactt ttaaaacccg gggtaactaa agaattgtct     300
ccgactataa acgtgaagcc ctcaactggc agtaatttaa gaagcaaata ttcacagagt     360
ttgtcagcta tgaaaagtaa gttactgcag caacagcaaa ccgcatcaga tcagactaca     420
acaccacatg tagcgcctgt taatagcgc                                       449
```

<210> SEQ ID NO 40
<211> LENGTH: 468
<212> TYPE: DNA
<213> ORGANISM: Artificial Sequence
<220> FEATURE:
<223> OTHER INFORMATION: heat shock 70-kDa protein cognate 3

```
<400> SEQUENCE: 40
gttacgagcc agggtgaaaa gatctttgcc cctgaagaaa tttctgccat ggtcttgggc        60
aaaatgaaag agactgctga agcttacctt ggtaaaaaag ttacccatgc tgttgtaaca       120
gtaccagcat atttcaatga tgctcagaga caggccacca aagacgccgg tgttattgct       180
ggacttaatg ttatgagaat tatcaatgaa cctacagctg ctgccattgc atatggtatg       240
gataagaaag aagggggaaaa gaatgtgtta gtctttgatt tgggtggtgg aacctttgat      300
gtttccctcc ttaccattga taatggagtc tttgaggtgg tggctacaaa tggtgacact       360
catttgggtg gcgaagactt cgatcagcgt gttatggacc actttatcaa gctgtacaaa       420
aagaagaagg gcaaagacat tcgcaaagat aaccgtgccg ttcaaaag                    468

<210> SEQ ID NO 41
<211> LENGTH: 442
<212> TYPE: DNA
<213> ORGANISM: Artificial Sequence
<220> FEATURE:
<223> OTHER INFORMATION: gawky dsRNA

<400> SEQUENCE: 41
caacattgcg ccgactacta cgaataataa tgttaacaat acgacttcaa cgaatacgac        60
caagcagcaa ttagagcagc tgaataatat gcgagaagct atctttagcc acgatggatg       120
gggaggccat attaatcaag atacgacgtg ggaaattccg ggaagtccgg agcctcccat       180
aaaattggat ggtacgaacg cgcctccttg gaaaccaaca gtcaacaatg ggacagaatt       240
atgggaagca aatttgcgta atggtggtca accacctcct caacccagc aaaaaacgcc        300 ttggggccac acaccattaa ccaatattgg cggcacatgg ggcgaagatg atgatgtcgc       360
ggatacctct aatgtgtgga cgggtgttcc atcaggacaa cagcaatggg gaaatacagg       420
aaacagtgga ggaggaatgt gg                                                442
```